US011337586B2

(12) United States Patent
Devaiah et al.

(10) Patent No.: US 11,337,586 B2
(45) Date of Patent: May 24, 2022

(54) RETRACTABLE ENDOSCOPIC SUCTION TUBE

(71) Applicants: TRUSTEES OF BOSTON UNIVERSITY, Boston, MA (US); BOSTON MEDICAL CENTER CORPORATION, Boston, MA (US); FRAUNHOFER USA, INC., Plymouth, MI (US)

(72) Inventors: Anand Devaiah, Chestnut Hill, MA (US); Andre Sharon, Newton, MA (US); Alexis Sauer-Budge, Lincoln, MA (US); Holger Wirz, Medford, MA (US); Yuzhang Yang, Allston, MA (US); Stephanus Johannes Marcellis Van Der Kemp, Hengelo (NL); Daniel Echeverria, Cambridge, MA (US)

(73) Assignees: TRUSTEES OF BOSTON UNIVERSITY, Boston, MA (US); BOSTON MEDICAL CENTER CORPORATION, Boston, MA (US); FRAUNHOFER USA, INC., Plymouth, MI (US)

( * ) Notice: Subject to any disclaimer, the term of this patent is extended or adjusted under 35 U.S.C. 154(b) by 253 days.

(21) Appl. No.: 15/565,991

(22) PCT Filed: Apr. 15, 2016

(86) PCT No.: PCT/US2016/027862
§ 371 (c)(1),
(2) Date: Oct. 12, 2017

(87) PCT Pub. No.: WO2016/168673
PCT Pub. Date: Oct. 20, 2016

(65) Prior Publication Data
US 2018/0110404 A1    Apr. 26, 2018

Related U.S. Application Data

(60) Provisional application No. 62/147,690, filed on Apr. 15, 2015.

(51) Int. Cl.
*A61B 1/00* (2006.01)
*A61B 1/015* (2006.01)
(Continued)

(52) U.S. Cl.
CPC ...... *A61B 1/00133* (2013.01); *A61B 1/00128* (2013.01); *A61B 1/00135* (2013.01);
(Continued)

(58) Field of Classification Search
CPC combination set(s) only.
See application file for complete search history.

(56) References Cited

U.S. PATENT DOCUMENTS 4,800,869 A * 1/1989 Nakajima ......... A61B 1/00068
                                                        600/158
5,441,503 A * 8/1995 Considine ......... A61B 18/1485
                                                        606/115

(Continued)

FOREIGN PATENT DOCUMENTS

EP       1355687 A2    10/2003
WO    2002/056942 A2    7/2002
(Continued)

OTHER PUBLICATIONS

Kubo et al., "Irrigation-suction straw sheath system for a rigid endoscope during endonasal endoscopic pituitary surgery", Minim Invas NeuroSurg 48(6):373-375 (2005).

*Primary Examiner* — Aaron B Fairchild
*Assistant Examiner* — Shankar Raj Ghimire
(74) *Attorney, Agent, or Firm* — Nixon Peabody LLP; Ronald I. Eisenstein; Nicole D. Kling

(57) ABSTRACT

Disclosed herein is an aspiration assembly for attaching to an endoscope. The aspiration assembly comprises an
(Continued)

extendable suction tube for aspirating an object (e.g., smoke, blood, blood clot, bone debris, or tissue debris) at or near a surgical site during an endoscopic surgery. The aspiration assembly can further comprise an irrigation tube for directing a fluid to the surgical site for cleaning the endoscope lens. By integrating an extendable suction tube with the endoscope, the technology described herein obviate the need for instrument switching and/or multiple surgeons during the surgery.

13 Claims, 37 Drawing Sheets

(51) Int. Cl.
    *A61B 1/12* (2006.01)
    *A61B 1/04* (2006.01)
    *A61B 1/06* (2006.01)
    *A61B 1/07* (2006.01)

(52) U.S. Cl.
    CPC ............... *A61B 1/015* (2013.01); *A61B 1/12* (2013.01); *A61B 1/042* (2013.01); *A61B 1/0669* (2013.01); *A61B 1/0676* (2013.01); *A61B 1/0684* (2013.01); *A61B 1/07* (2013.01)

(56) References Cited

U.S. PATENT DOCUMENTS

| | | | |
|---|---|---|---|
| 6,086,530 A | 7/2000 | Mack | |
| 6,190,330 B1* | 2/2001 | Harhen | A61B 10/0283 600/566 |
| 8,518,055 B1* | 8/2013 | Cardinale | A61B 17/0682 606/139 |
| 8,529,439 B2* | 9/2013 | Ito | A61B 1/012 600/112 |
| 9,451,951 B2* | 9/2016 | Sullivan | A61B 17/0485 |
| 9,968,249 B2* | 5/2018 | Huang | A61B 1/317 |
| 2002/0082475 A1 | 6/2002 | Stahl et al. | |
| 2003/0122374 A1* | 7/2003 | Ouchi | A61B 1/00142 285/124.1 |
| 2003/0187461 A1* | 10/2003 | Chin | A61B 17/00008 606/129 |
| 2004/0182393 A1 | 9/2004 | MacMillan et al. | |
| 2005/0215856 A1* | 9/2005 | Fujikura | A61B 1/00082 600/116 |
| 2006/0264992 A1 | 11/2006 | Franer et al. | |
| 2009/0287043 A1* | 11/2009 | Naito | A61B 1/0052 600/104 |
| 2010/0048992 A1* | 2/2010 | Okada | A61B 1/00071 600/106 |
| 2011/0092892 A1* | 4/2011 | Nitsan | A61B 1/00068 604/28 |
| 2012/0004503 A1* | 1/2012 | Kawaura | A61B 1/00087 600/104 |
| 2012/0029429 A1 | 2/2012 | Klein | |
| 2012/0078038 A1* | 3/2012 | Sahney | A61B 1/303 600/104 |
| 2013/0218149 A1* | 8/2013 | Braun | A61B 1/00082 606/21 |
| 2014/0150782 A1* | 6/2014 | Vazales | A61M 16/0463 128/202.16 |
| 2014/0221750 A1 | 8/2014 | Weitzner | |
| 2014/0296633 A1 | 10/2014 | Gumbs | |
| 2016/0120395 A1* | 5/2016 | Qi | A61B 1/00135 600/123 |
| 2016/0143511 A1* | 5/2016 | Cheng | A61B 1/00066 600/123 |
| 2017/0079520 A1* | 3/2017 | Huang | A61B 1/317 |
| 2017/0105602 A1* | 4/2017 | Fujitani | G02B 23/24 |
| 2018/0228947 A1* | 8/2018 | Woolford | A61B 1/126 |
| 2018/0235441 A1* | 8/2018 | Huang | A61B 1/317 |

FOREIGN PATENT DOCUMENTS

| | | | |
|---|---|---|---|
| WO | 2006/014814 A1 | 2/2006 | |
| WO | WO-2006014814 A1 * | 2/2006 | ......... A61B 1/00142 |
| WO | 2014/151938 A2 | 9/2014 | |
| WO | WO-2015120348 A1 * | 8/2015 | ........... A61B 5/0071 |

* cited by examiner

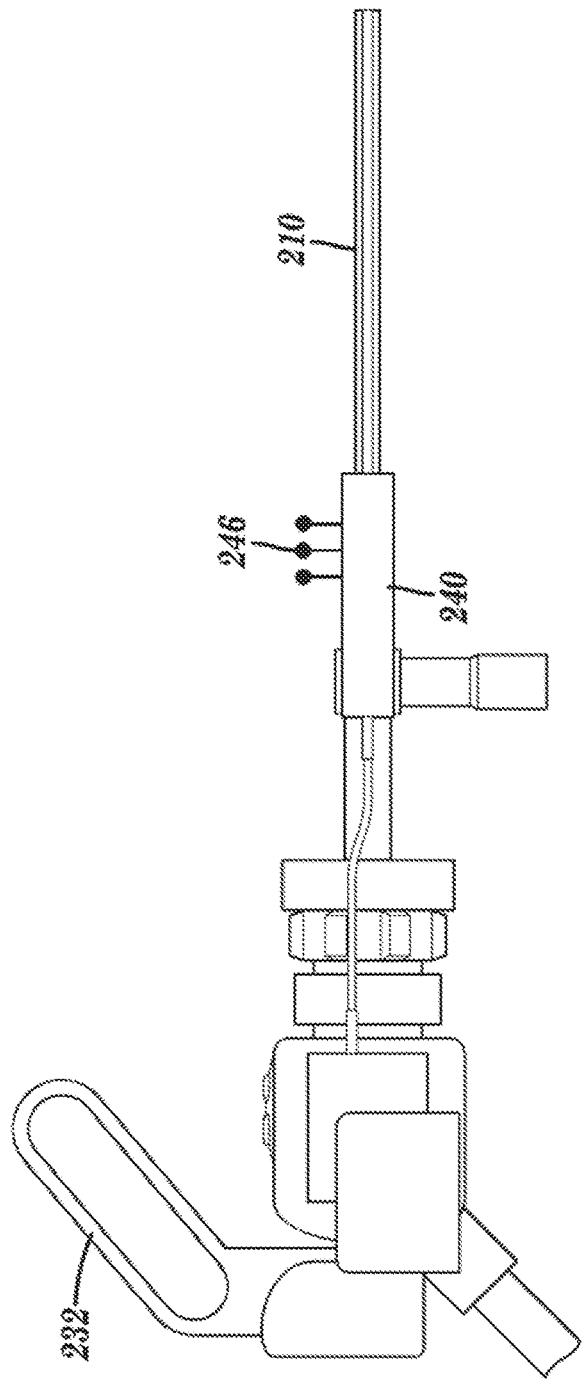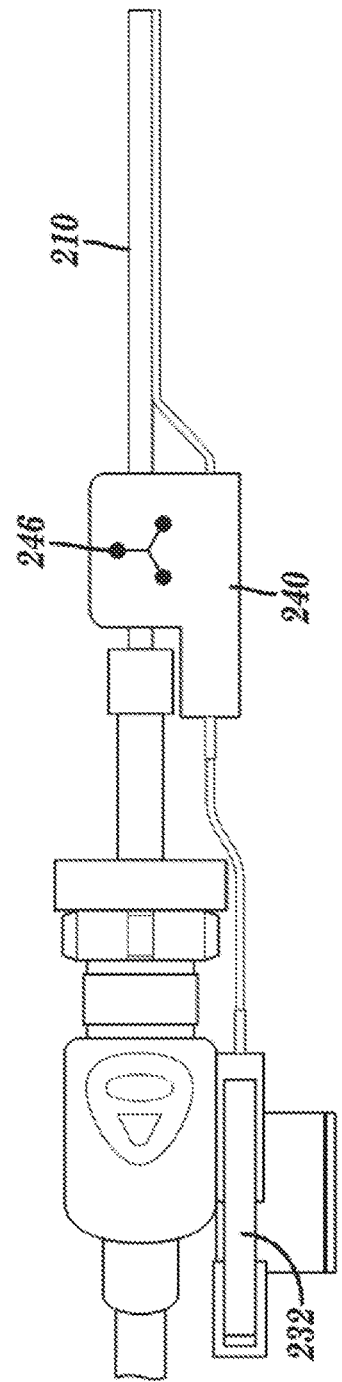
FIG. 2B
FIG. 2C

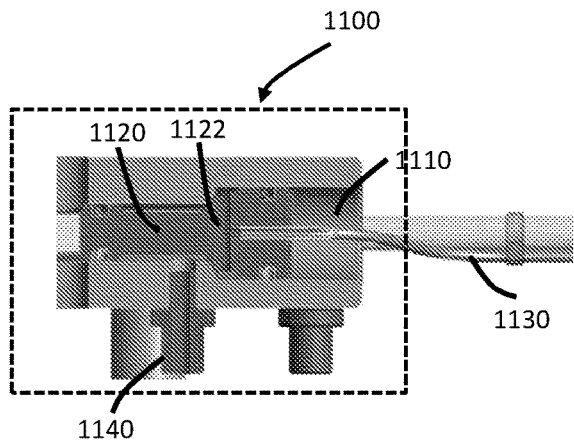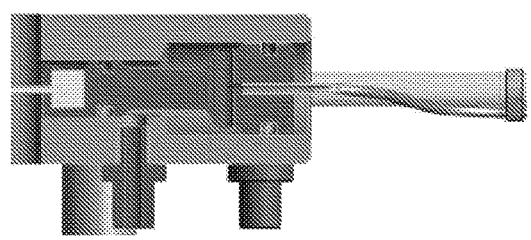
FIG. 11A  FIG. 11B
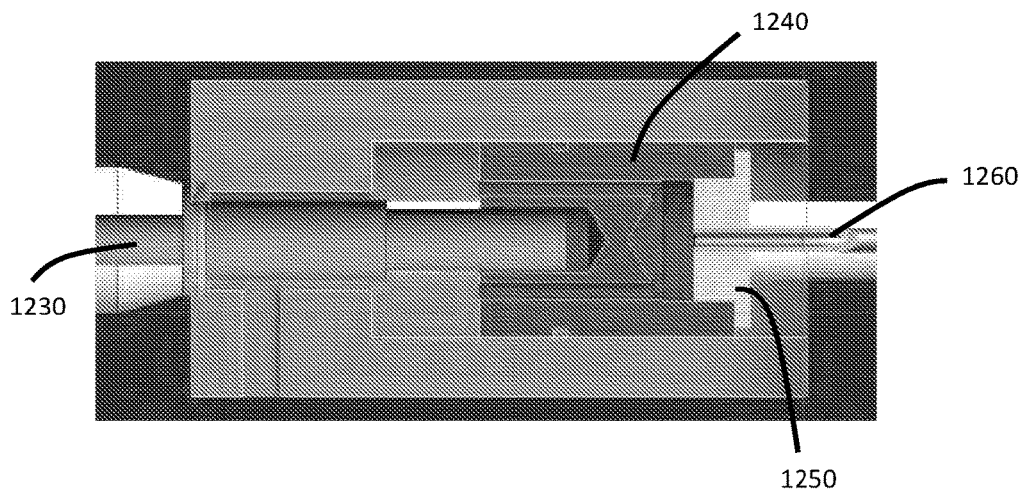
FIG. 12

Endoscope 202

Retractable Suction Tube 220

Guide Clip 222

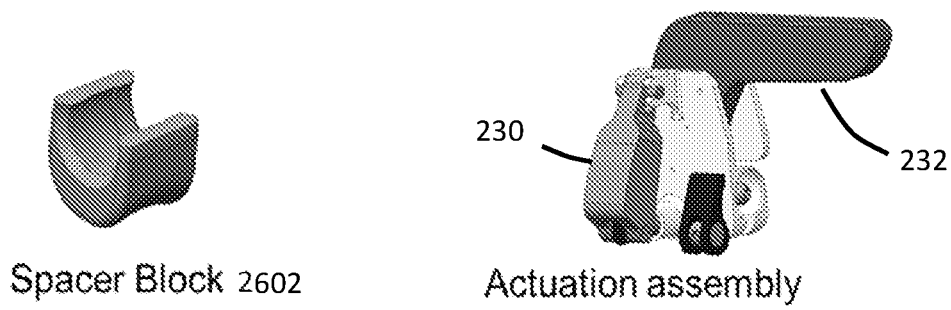
Spacer Block 2602
FIG. 20A
Actuation assembly
FIG. 20B
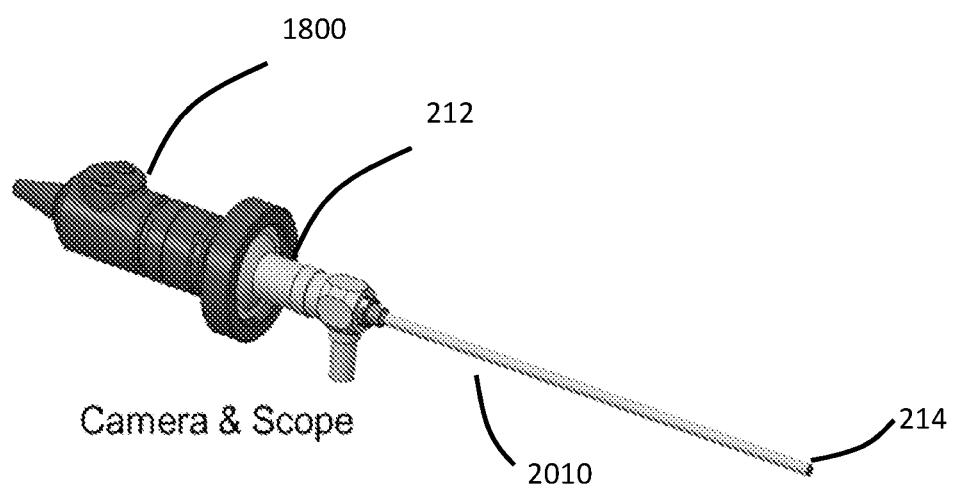
Camera & Scope
FIG. 20C
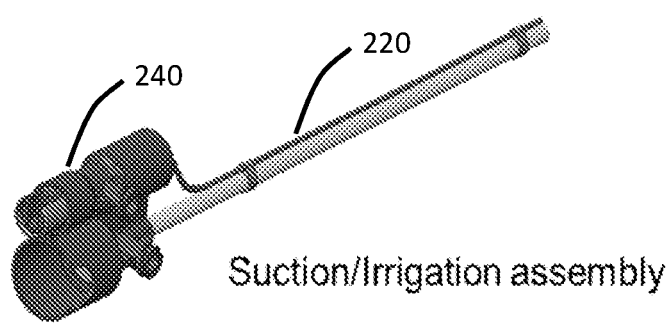
Suction/Irrigation assembly
FIG. 20D

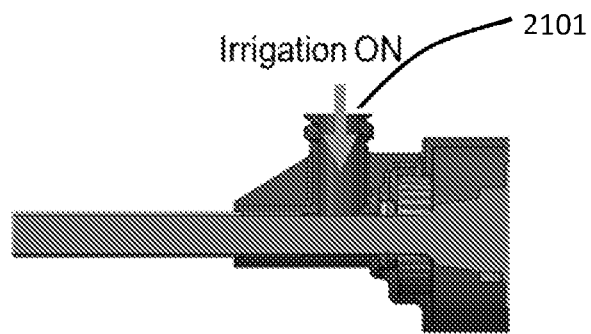
FIG. 21A
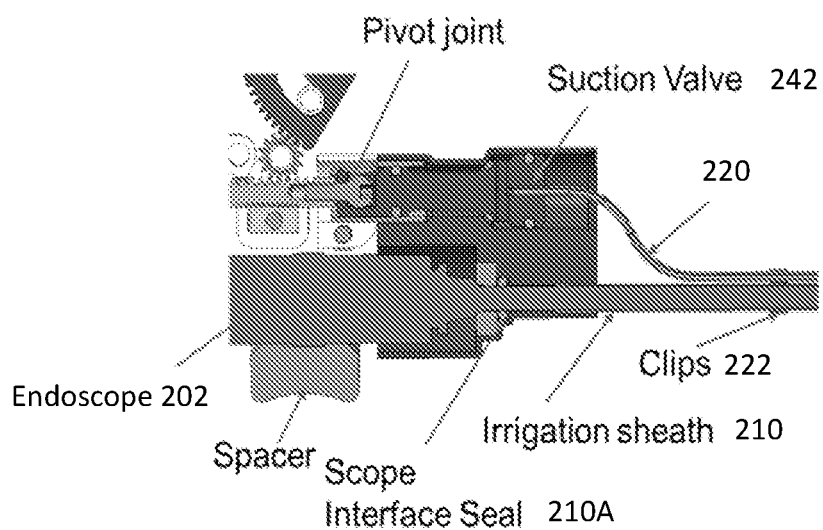
FIG. 21B
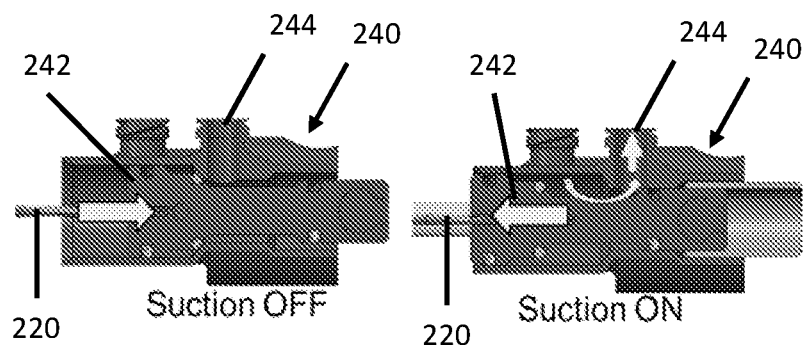
FIG. 21C  FIG. 21D

Cam Clamp

Side Position of Handle

Above Positioning of handle

Side Position of Handle

Above Positioning of handle

Vertical Position of Handle

Side Position of Handle

Side Position of Handle

Angled Right

Angled Left

Vertical Position of Handle

RETRACTABLE ENDOSCOPIC SUCTION TUBE

CROSS-REFERENCE TO RELATED APPLICATIONS

This application is a 35 U.S.C. § 371 National Phase Entry Application of International Application No. PCT/US2016/027862 filed Apr. 15, 2016, which designates the U.S. and claims benefit under 35 U.S.C. § 119(e) of U.S. Provisional Application No. 62/147,690 filed Apr. 15, 2015, the contents of which are incorporated herein by reference in their entireties.

TECHNICAL FIELD

The present invention relates to aspiration systems for endoscopes and more particularly to user extendable aspiration systems for endoscopes.

BACKGROUND

An endoscope is a tool that allows a physician to take a look inside a patient's body, and is widely used in medicine for diagnosis and surgery. Especially in minimally invasive surgery (MIS), endoscopes are essential tools. They consist of a flexible or rigid tube with a lens on one end and an eyepiece on the other. Inside the tube there is an optical system and light delivery system. The light delivery system usually consists out of a bundle of optical fibers that transport light from an external light source to the endoscope's tip to illuminate the area it is pointed at. The optical system transports the objective lens image to the eyepiece, in a rigid endoscope this is done by a system of relay lenses and in a flexible endoscope with a bundle of optic fibers.

A clear view through the endoscope is very important for the surgeon to be able to perform tasks effectively and safely. Whenever the endoscope's vision is impaired the surgeon is forced to pause and restore the view before continuing. During a procedure a surgeon may need to use cutting tools, hot wire, lasers or even small milling tools to perform the surgery. This often causes bleeding, smoke or bone dust which can obscure the endoscope's view in three ways: (1) blood, bone dust or other material gets on the lens of the endoscope, blurring or blocking the view; (2) bone dust or smoke fills the air in front of the endoscope's lens, fogging or blocking the view; (3) the area the surgeon wants to see is covered with blood, bone dust and/or irrigation fluid, making it hard or impossible to distinguish shapes and colors. To be able to quickly remove solid or liquid debris obscuring the view of the endoscope lens, remove smoke, or to clean up a blood-covered area, surgeons can use a suction-irrigation sheath as displayed in FIG. 1.

Most of these removable sheaths slide over the endoscope and are connected to a vacuum and irrigation system. Irrigation fluid flows between the inner surface of the sheath and the outer surface of the endoscope and from the proximal end of the endoscope to the distal end of the endoscope, allowing the irrigation fluid to irrigate the area in view or in some cases rinse the lens. A suction channel is integrated into the sheath that can remove smoke or dust from the surgical site and can clean up accumulated blood or tissue by pressing the tip into it. This means that there is no need for a surgeon to remove the endoscope every time the lens gets dirty or to use a separate suction tool to clean up excess blood. Sheaths like these are commonly used as they allow surgeons to perform endoscopic surgeries more efficiently and thus more quickly.

However, all of these aspiration systems have a shared shortcoming: having to move the endoscope tip into the matter that needs to be removed could cause the surgeon's view to obscured by the tissue as well as blood or other matter.

Accordingly, there exists in the art a need for novel aspiration systems for endoscopes.

SUMMARY

The technology described herein provides an endoscopic aspiration system that overcomes the above-identified shortcoming of existing devices. Specifically, the endoscopic system according to the invention comprises an extendable aspirator or suction tube that can extend or retract under user control. When the suction tube is extended, the suction tube is connected to a vacuum source, thus permitting the suction tube to aspirate an object close to the distal end of the suction tube. When the suction tube is retracted, the suction tube is automatically disconnected from the vacuum source. The endoscopic aspiration assembly can also comprise an irrigation tube for directing a fluid to the viewing end of the endoscope.

One aspect of the technology described herein relates to an aspiration assembly adapted to be attached to an endoscope, wherein the endoscope comprises a tubular member or shaft that extends from the proximal end to the distal end and visualization system. Some endoscopes can include a working channel extending through a tubular member from a proximal end to a distal end of the endoscope. The visualization system can include either an optical system extending through the shaft or a camera mounted at the distal end of the shaft that is configured to provide images of a field of view at the distal end of the endoscope. Where the endoscope includes an optical system, a lens is provided at the distal end and an eye piece is provided at the proximal end and a camera can be fitted to the eye piece to transmit the images to a presentation screen positioned for easy viewing by the user. Where the endoscope includes a camera at the distal end of the shaft, a cable running through the shaft carries the images to a presentation screen positioned for easy viewing by the user. The aspiration assembly can include an extendable suction tube configured to be coupled to the tubular member and move axially, parallel to the tubular member, beyond the distal end of the endoscope; and an actuator configured to be coupled to the suction tube and extend or retract the suction tube with respect to the distal end of the endoscope when the actuator is actuated.

In accordance with some embodiments of the invention, the suction tube can be connected to a vacuum source when the suction tube is extended and the suction tube can be disconnected from the vacuum source when the suction tube is retracted.

In accordance with some embodiments of the invention, the suction tube has an opening at a distal end of the suction tube adapted to aspirate solid or liquid debris selected from the group consisting of blood, an irrigation fluid, a blood clot, a bone fragment, and a tissue fragment. The suction tube can also be adapted to aspirate smoke from a surgical site.

In accordance with some embodiments of the invention, the distal end of the suction tube can be positioned within the field of view of the endoscope when the suction tube is at least partially extended.

In accordance with some embodiments of the invention, the actuator comprises a handle portion coupled to the suction tube and configured to extend or retract the suction tube by actuation of the handle portion.

In accordance with some embodiments of the invention, the handle portion comprises a movable handle configured to extend or retract the suction tube when the movable handle is actuated.

In accordance with some embodiments of the invention, the actuator comprises a first gear coupled to a second gear of the movable handle, and a gear rack coupled to the first gear, thereby converting a rotary handle motion to a linear motion of the suction tube.

In accordance with some embodiments of the invention, the actuator comprises a locking mechanism configured to lock the suction tube at a fixed position.

In accordance with some embodiments of the invention, the locking mechanism comprises a pair of gear racks configured to intermesh to lock the suction tube at a fixed position.

In accordance with some embodiments of the invention, the actuator comprises a safety button configured to unlock the locking mechanism when the safety button is actuated, thereby permitting the movement of the suction tube.

In accordance with some embodiments of the invention, the actuator further comprises a push-pull cable coupled to the handle portion and the suction tube, whereby the handle portion actuates the push-pull cable to extend or retract the suction tube.

In accordance with some embodiments of the invention, the actuator is coupled to the suction tube through a suction control mechanism.

In accordance with some embodiments of the invention, the actuator is adapted to be detachable from the suction control mechanism.

In accordance with some embodiments of the invention, the suction control mechanism comprises a piston coupled to the vacuum source and the suction tube.

In accordance with some embodiments of the invention, the suction tube is configured to be attached to the tubular member through one or more clips.

In accordance with some embodiments of the invention, the actuator is configured to be attached to the proximal end of the endoscope or to a camera attached to the proximal end of the endoscope using a latching mechanism.

In accordance with some embodiments of the invention, the aspiration assembly further comprises an irrigation tube configured to extend along the tubular member of the endoscope and direct a fluid from a fluid source to the proximity of the distal end of the endoscope.

In accordance with some embodiments of the invention, the irrigation tube is configured to enclose the tubular member of the endoscope, whereby the fluid flows on the outside of the tubular member.

In accordance with some embodiments of the invention, the irrigation tube is configured to fit inside the tubular member of the endoscope.

In accordance with some embodiments of the invention, the tubular member of the endoscope is rigid.

In accordance with some embodiments of the invention, the suction tube is connected to a vacuum source, regardless whether the suction tube is extended or retracted.

In accordance with some embodiments of the invention, the actuator can comprise a motor.

In accordance with some embodiments of the invention, the actuator can comprise a pneumatic actuator.

In accordance with some embodiments of the invention, the actuator can comprise a hydraulic actuator.

The aspiration assembly can be attached to an existing endoscope and permits easy exchange of the endoscope. In some embodiments, a portion of the aspiration assembly can be disposable. The aspiration assembly can be used in a variety of endoscopic procedures such as laparoscopic and arthroscopic operations.

BRIEF DESCRIPTION OF THE DRAWINGS

FIGS. 2A, 2B and 2C show an isometric view, a side view and a top view, respectively, of an endoscope having an aspiration assembly attached thereon in accordance with some embodiments of the invention.

FIGS. 11A-11B are illustrations of a shut-off valve in accordance with some embodiments of the invention. (FIG. 11A) The suction tube 1130 is disconnected from the vacuum source. (FIG. 11B) The suction tube 1130 is connected to the vacuum source.

FIG. 12 is an illustration of integrated suction shut-off system in the actuator in accordance with some embodiments of the invention.

FIG. 14A shows the push-pull cable in the retracted position; FIG. 14B shows an isometric view of the push-pull cable in the retracted position; and FIG. 14C shows the push-pull cable in the extended position.

FIG. 15A shows the over-center locking system in the open position and FIG. 15B shows the over-center locking system in the closed or locked position.

FIG. 16A is a photograph showing one view of the endoscope having the aspiration assembly attached thereon. FIG. 16B is a photograph showing another view of the endoscope having the aspiration assembly attached thereon. FIG. 16C is a schematic showing the cross section of the distal end of the endoscope. FIG. 16D is a schematic showing a side view of the distal end of the endoscope.

FIG. 19B shows an embodiment with the Olympus OTV-S7 camera, which is small compared to the Karl Storz H3-Z camera shown in FIG. 19A. The red arrows indicate difference in size and geometry from the Olympus and Karl Storz camera, illustrating the underlying motivation for the different embodiments described herein, e.g., different sizes and larger ranges of compatibility with various cameras.

FIGS. 20A, 20B, 20C, 20D depict illustrations of the main components of the endoscopic aspiration systems described herein. FIG. 20A shows a spacer block; FIG. 20B shows the actuator assembly; FIG. 20C shows the camera and scope assembly; and FIG. 20D shows the suction/irrigation assembly.

FIGS. 21A, 21B, 21C, 21D depict illustrations of the internal suction and irrigation elements of certain embodiments described herein. FIG. 21A shows the irrigation flow when the irrigation is on; FIG. 21B shows a cross-section view of the suction valve in the actuator assembly; FIG. 21C shows the suction valve in the suction off position; FIG. 21D shows the suction valve in the suction on position.

FIG. 24B shows the visualization system (camera) and endoscope, depicting their relation to each other, while FIG. 24A shows how the visualization system and endoscope combination are arranged according to one embodiment of the endoscopic aspiration system.

FIG. 25A show the over-molded components of the irrigation tube assembly; FIG. 25B shows the over-molded O-ring seals on the suction valve connected to the retractable suction tube; FIG. 25C shows the molded suction guide 222 elements; and FIG. 25D shows the components of an actuator assembly according to some embodiments of the invention.

As shown in FIG. 26A, one or more spacers 2602 can be added opposite to the handle to provide ergonomic adjustment to accommodate different sized hands. As shown in FIG. 26A, the suction tube can be moved axially to various positions with respect to the endoscope. As shown in FIG. 26C, the retractable suction tube can be mounted on guide elements 222 that can be rotated around the endoscope to re-direct suction circumferentially. FIG. 26B shows the seals 5 inside the suction valve manifold that permit suction to continue at various suction tube positions, while preventing fluids from escaping the device. FIG. 26D shows the interface seal that prevents irrigation fluid from leaking from the proximal end of the endoscope.

FIG. 27A shows the handle mechanism can be configured such that release of the handle automatically causes retraction of the suction tube if the safety button 230 is depressed. FIG. 27B shows handle mechanism can be configured such that the suction tube can be locked at various axial positions. The large teeth provide strength and power to move the suction tube, while the smaller opposing teeth provide greater resolution for locking the position of the suction tube.

DETAILED DESCRIPTION

Aspects and embodiments of the invention relate to an aspiration assembly and an endoscope including an extendable aspiration tube. The aspiration assembly comprises an extendable suction tube, and can be attached to a commercially available endoscope. Under a user's command, the suction tube can be extended or retracted relative to the endoscope's distal end for aspirating smoke, or solid or liquid debris from a surgical site such as blood, an irrigation fluid, Cerebral Spinal fluid, transudate, exudate, mucous, a blood clot, bone fragments, or tissue fragments that can obscure the field of view. In addition, the amount of extension can be controlled by the user.

The aspiration assembly according to the invention permits a single user to operate the endoscope and perform suction and lens cleaning without the need of multiple users or switching instruments. Moreover, because the suction tube is extendable, there is no need to move the endoscope tip into the matter that needs to be removed. Instead, the suction tube can be extended towards the matter for removal, thereby keeping the surgical site in the field of view.

According to the invention, some embodiments of the endoscopes having the aspiration assembly attached thereon are shown in FIGS. 2, 3, and 4A-4C.

Figure 1:
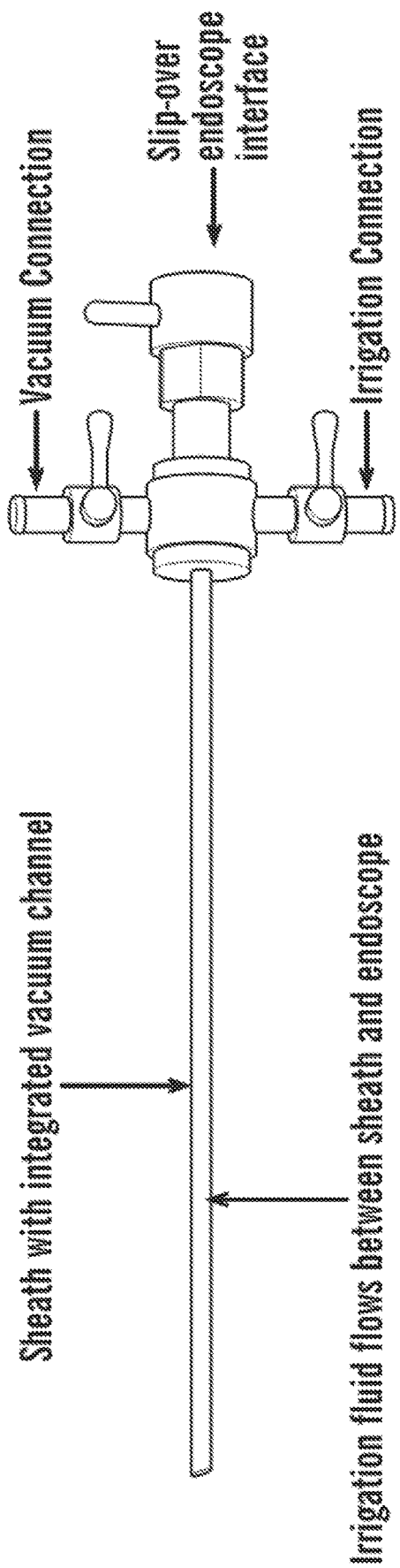
FIG. 1 is an image of a stainless steel suction-irrigation sheath for endoscopes in the prior art.
Figure 2A:
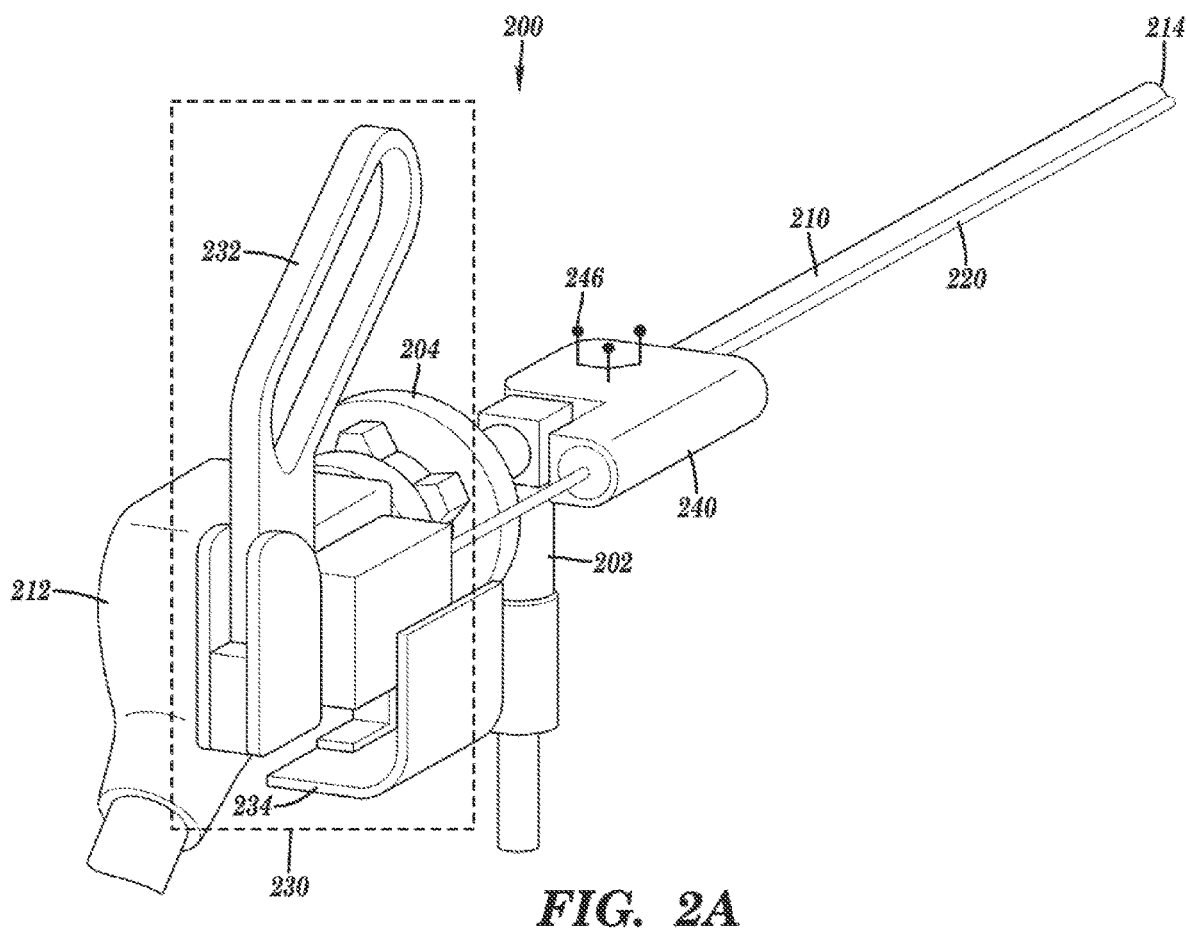

FIG. 2 shows an endoscopic system 200 in accordance with some embodiments of the invention. The endoscopic system 200 can comprise a sheath 210 encircling the tubular member or shaft of an endoscope 202 that can extend from a proximal end 212 to a distal end 214 of the endoscope 202, and a visualization system inside the endoscope 202, that is configured to transmit a field of view from the distal end 214 to the proximal end 212 of the endoscope 202. The visualization system can include a camera 204 mounted to the proximal end 212 of the endoscope to enable images of the field of view to be displayed on a display screen to the user. Visualization systems for endoscopes are known to those skilled in the art and are not discussed in detail here. As used herein, "proximal" means closest to the surgeon and farthest from the surgical site, while "distal" means farthest from the surgeon and closest to the surgical site. The endoscope 200 can further comprise an extendable suction tube 220 extending parallel to the sheath 210, the suction tube 220 being able to extend or retract relative to the distal end 214. The length of the suction tube 220 can be similar to the length of the sheath 210. The suction tube 220 can be connected to a vacuum source when the suction tube 220 is extended and disconnected from the vacuum source when the suction tube 220 is retracted. In some embodiments, the endoscopic system 200 does not include the sheath 210 and the suction tube 220 extends parallel to the tubular member or shaft of the endoscope and can be configured to extend or retract relative to the distal end 214 of the endoscope shaft.

In some embodiments, the suction tube 220 can be calibrated to an image guidance system and modified to act as a probe for image guided surgery. The distal end of the suction tube, as it extends and retracts, can act as the probe tip for stereotactic target tissue localization as performed with the image guidance system. In some embodiments, the translation of this distal suction tube movement into stereotactic localization will be integrated into the device, in others it can be enabled by attaching or incorporating a reference array or image guidance system adapter 246 into the endoscopic system 200. The reference array can be positioned at a predefined distance from the distal end of the suction tube in order to be calibrated as a probe for the image guidance system. In this configuration, a representation of the suction tube can be inserted into the images used in image guided surgery.

The endoscopic system 200 can further comprise an actuator 230 coupled to the suction tube 220 and the proximal end 212 of the endoscope 202 or the camera 204. When the actuator 230 is actuated, the actuator 230 can be adapted to extend or retract the suction tube 220 with respect to the distal end 214.

Figure 6:
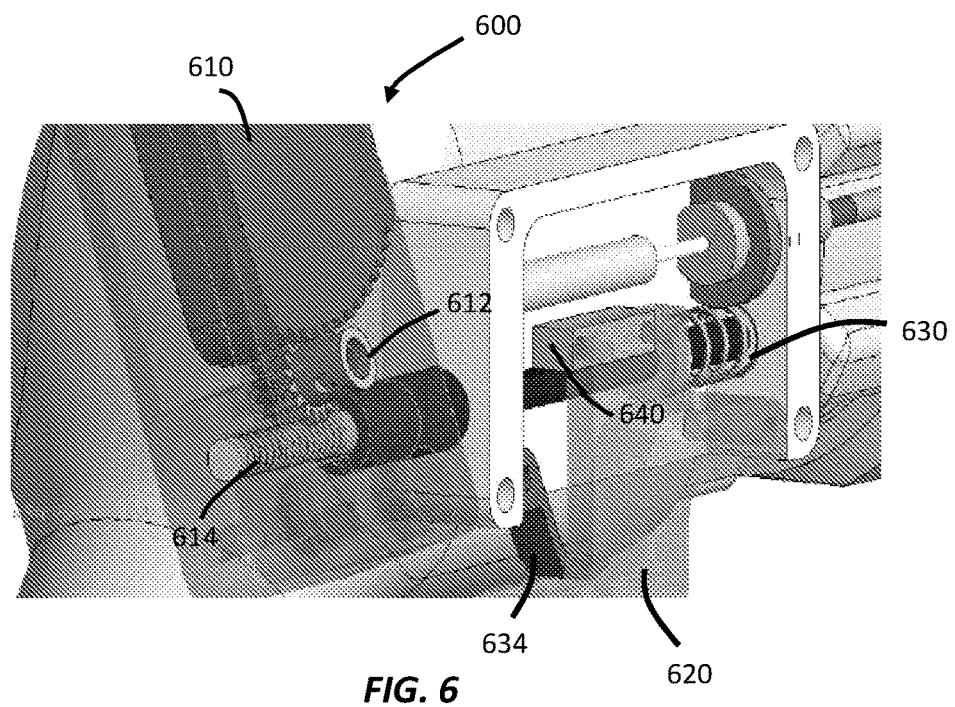
FIG. 6 is an illustration of a system of gears and a gear rack in an actuator in accordance with some embodiments of the invention.

The actuator 230 can further comprise a handle portion 232, which serves as an interface for a user to control the movement of the suction tube 220. For example, the user can exert a predetermined amount of pressure or movement on the handle portion 232 to extend or retract the suction tube 220 by a controlled distance. In accordance with some embodiments of the invention, the handle portion 232 can comprise a movable handle (e.g., a rotary handle) that can extend or retract the suction tube 220 when the movable handle is actuated. For example, when the movable handle is moved in one direction, the suction tube 220 is extended; when the movable handle is moved in an opposite direction, the suction tube 220 is retracted. The amount of the movement of the movable handle can determine how much the suction tube 220 is extended or retracted. In accordance with some embodiments of the invention, the handle portion 232 has an ergonomic design. As used herein, the term "ergonomic" is defined broadly herein to mean having one or more design features intended to promote comfort and fit of the hand holding a device, e.g., to reduce fatigue and improve control. In some embodiments, the handle portion 232 of the actuator 230 and/or the actuator 230 can be positioned in different angular orientations with respect to the longitudinal axis of the endoscopic system 200, for example, see FIGS. 6, 28A, 28B, 28C, 28D, 29A, 29B, 29C, 30A, 30B, and 30C. FIG. 6 depicts one embodiment of a mechanism that permits adjustment of the angular orientation of the handle portion 610. In this embodiment, the handle portion 610 can be mounted to a post or drive rod 614 and permitted to rotate or pivot around the post 614 to be configured in different angular positions around the post 614 to accommodate the needs of the surgeon. Alternatively, the handle 232 and/or the actuator assembly 230 can be oriented in a pistol grip configuration. FIGS. 28A, 28B, 28C, 28D, 29A, 29B, 29C, 30A, 30B, and 30C depict alternative possible positions of the handle.

In accordance with some embodiments of the invention, the actuator 230 can comprise one or more buttons adapted to extend or retract the suction tube 220. The one or more buttons can be connected to an electrical circuit controlling an electrical actuator, such as a motor, that is coupled to the suction tube 220. For example, actuating one button can provide a first signal to the electrical circuit to extend the suction tube 220, while actuating another button can provide a second signal to the electrical circuit to retract the suction tube 220. It is contemplated that a single button can be designed to permit both tube extension and retraction.

In accordance with some embodiments of the invention, the actuator 230 can comprise a pneumatic actuator. A pneumatic actuator converts energy (typically in the form of compressed air) into mechanical motion. A pneumatic actuator generally comprises a piston that is movable inside a cylinder, and valves or ports. In some embodiments, the pneumatic actuator includes a diaphragm that moves in response to pneumatic pressure. The pneumatic actuator can be coupled to the suction tube 220 such that the mechanical motion of the actuator can extend or retract the suction tube 220. Non-limiting examples of pneumatic actuators include tie rod cylinders, rotary actuators, grippers, rodless actuators with magnetic linkage or rotary cylinders, rodless actuators with mechanical linkage, pneumatic artificial muscles, and vacuum generators.

In accordance with some embodiments of the invention, the actuator 230 can comprise a hydraulic cylinder coupled to the suction tube 220. A hydraulic cylinder (also called a linear hydraulic motor) is a mechanical actuator that can give a unidirectional force through a unidirectional stroke. There are two types of hydraulic cylinders: tie rod cylinders and welded body cylinders.

Figure 5:
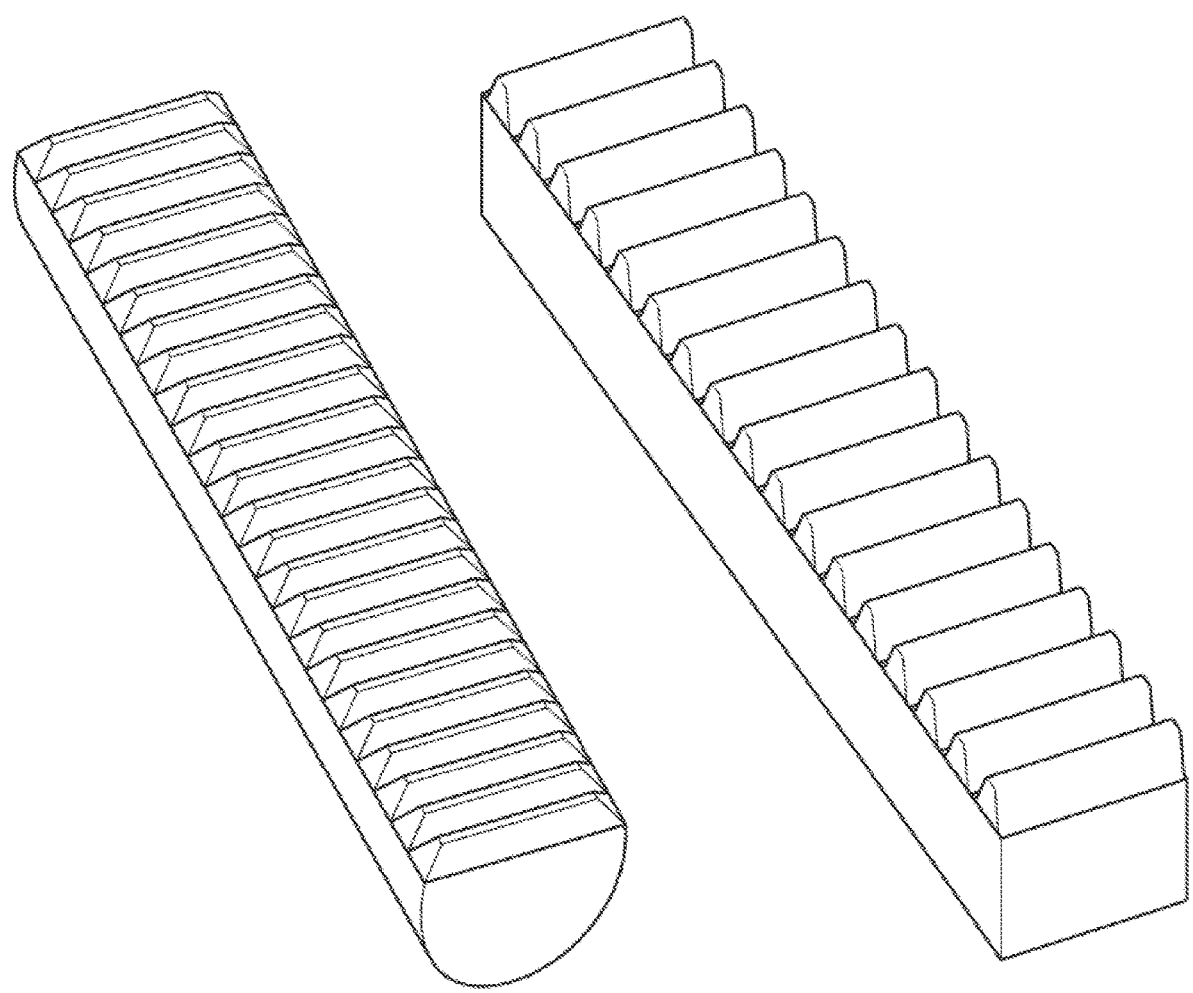
FIG. 5 is an illustration of round and rectangular gear racks that can be used in the locking mechanism.

In accordance with some embodiments of the invention, the actuator 230 can further comprise a locking mechanism configured to lock the suction tube 220 at a fixed position. The locking mechanism can be coupled to a safety button 234 which can be configured to unlock the locking mechanism when the safety button 234 is actuated, such that the movement of the suction tube 220 is allowed. In accordance with some embodiments of the invention, the locking mechanism can comprise a pair of gear racks such as shown in FIG. 5 that can intermesh to lock the suction tube 220. In accordance with some embodiments of the invention, the locking mechanism can comprise a friction system. A friction system can take advantage of friction to lock the suction tube 220 by pushing two surfaces together. An example of a friction system is shown in In FIG. 10B.

Figure 27A:
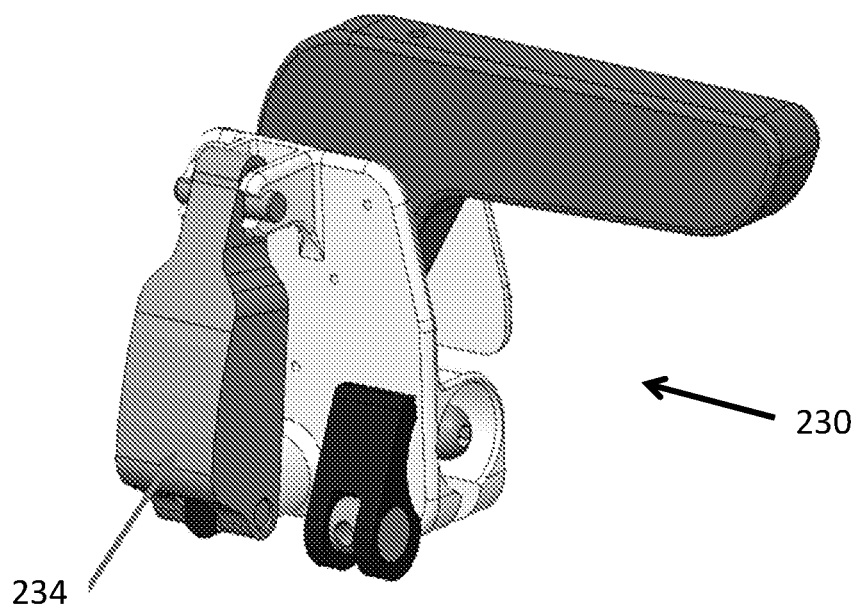
FIGS. 27A and 27B depict illustrations of certain embodiments of the handle mechanism.
Figure 27B:
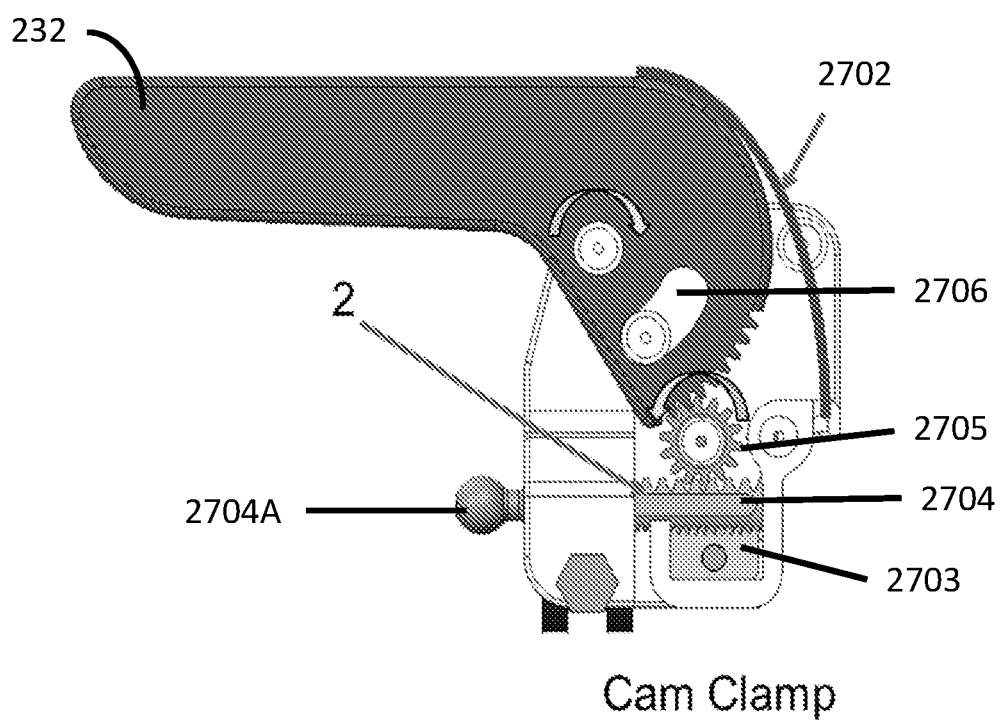
Figure 28A:
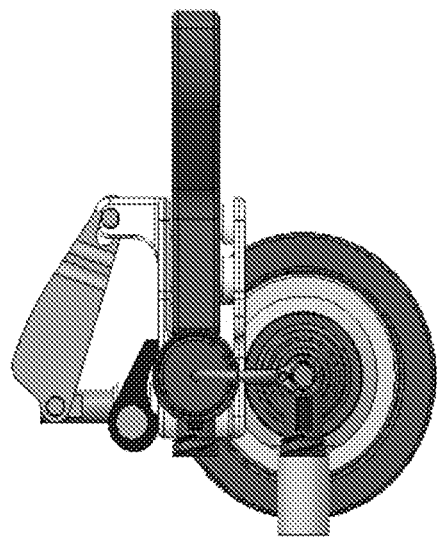
FIG. 28A shows an end view of the handle and actuator assembly in the side position and FIG. 28B shows an end view of the handle and the actuator assembly positioned above the endoscope.
Figure 28B:
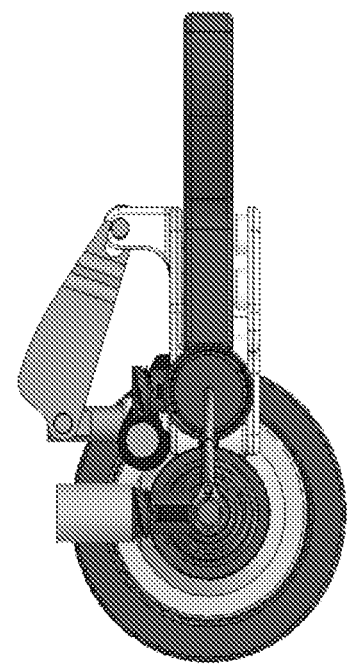
Figure 28C:
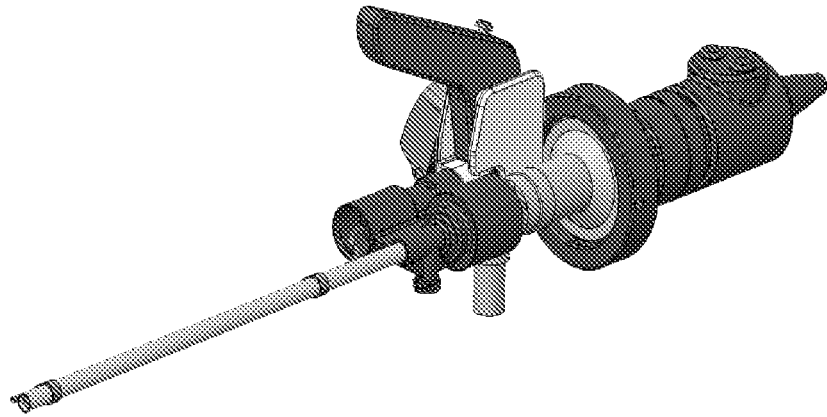
FIG. 28C shows an isometric view of the handle and actuator assembly in the side position and FIG. 28D shows an isometric view of the handle and the actuator assembly positioned above the endoscope.
Figure 28D:
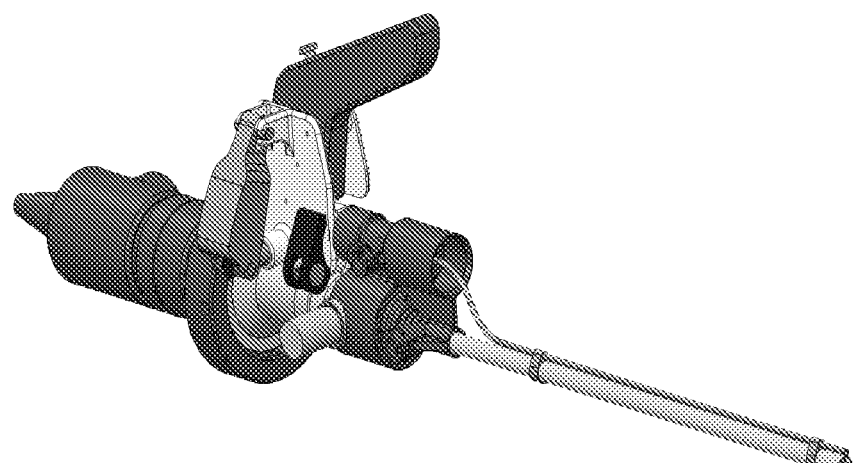
Figure 29A:
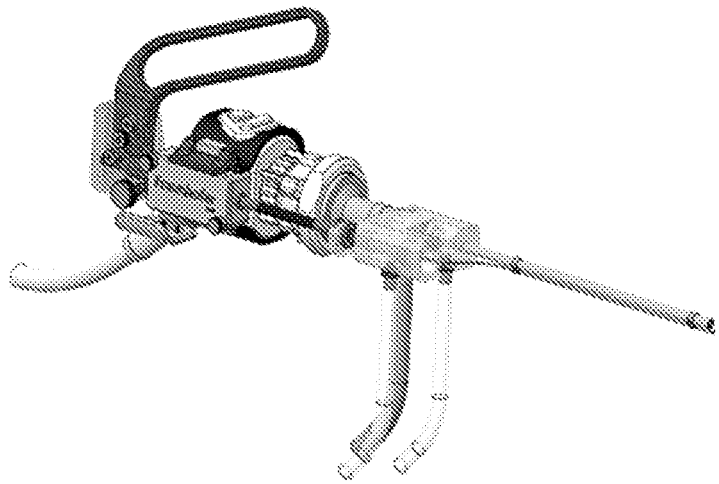
FIG. 29A shows an isometric view of the handle in the vertical position.
Figure 29B:
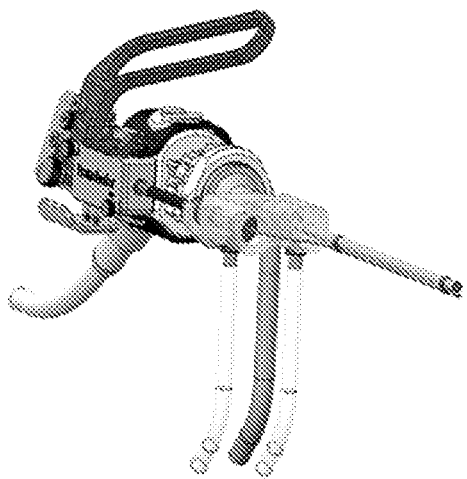
FIG. 29B shows an isometric view of the handle in one side position.
Figure 29C:
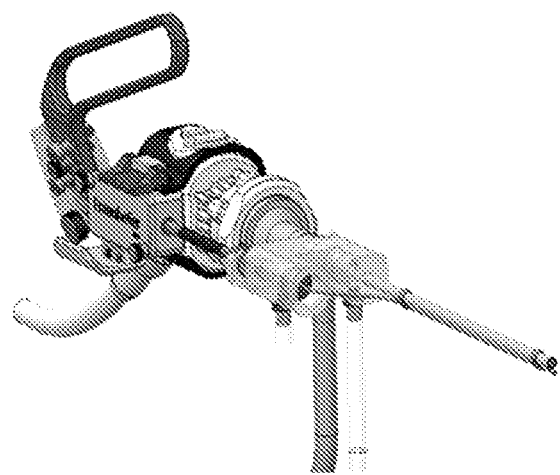
FIG. 29C shows an isometric view of the handle in another side position.
Figure 30A:
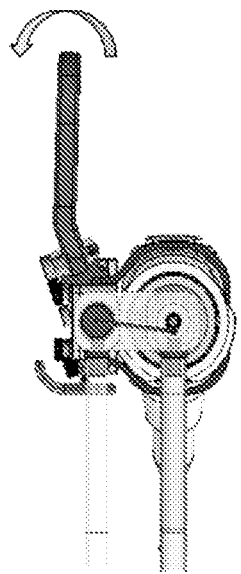
FIG. 30A shows an end view of the handle angled right.
Figure 30B:
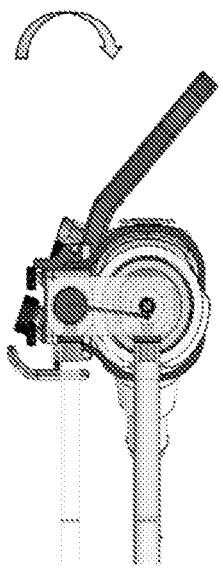
FIG. 30B shows an end view of the handle angled left.
Figure 30C:
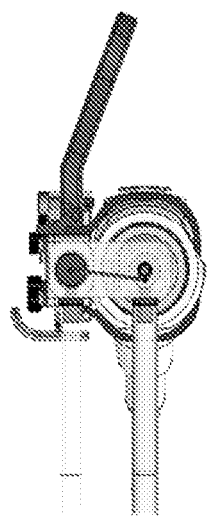
FIG. 30C shows the handle in the vertical position.

In accordance with some embodiments of the invention and as depicted in FIGS. 27A and 27B, the handle mechanism of the actuator 230 can be configured such that release of the handle automatically causes retraction of the suction tube 220. In accordance with some embodiments of the invention the handle portion 232 can be configured such that release of the handle portion 232 automatically causes retraction of the suction tube 220 if the safety button 234 is actuated, e.g., as depicted in FIG. 27B. For example, as shown in FIG. 27B, a rubber strap or coil spring 2702 can be attached to the handle portion 232 such that the rubber strap or coil spring 2702 is extended as the lever is depressed, thereby storing potential energy that is translated into motion once the lock mechanism is released. An alternative embodiment of such an automatic retraction device is depicted in FIG. 6, where the spring 630 serves to store the potential energy as the handle portion is moved.

In accordance with some embodiments of the invention, the actuator can include a motor, a pneumatic cylinder or a hydraulic actuator that is configured to apply a force against the locking mechanism such that when the locking mechanism is released, the actuator retracts the suction tube 220. The motor can be driven in a direction that causes the suction tube 220 to retract when the locking mechanism is released. The pneumatic cylinder can be positively or negative pressurized to retract the suction tube 220 when the locking mechanism is released. The hydraulic actuator can be actuated in the direction to retract the suction tube 220 when the locking mechanism is released.

In accordance with some embodiments of the invention, the actuator 230 can further comprise a locking mechanism configured to lock the suction tube 220 at a fixed axial position. One embodiment is depicted in FIG. 27B, wherein the large teeth depicted provide strength and power, while the smaller opposing teeth provide greater resolution for positioning of the suction tube 220. When the handle portion 232 is pressed down to any position (as depicted in FIG. 27B), this causes the suction tube to extend. The rubber strap or coil 2702 also becomes extended at the same time. If the safety button 234 is accidently or intentionally pressed, the lock block 2703 moves to release the connecting drive rod 2704 (this process is also illustrated in FIG. 22B). The handle portion 232 rotates about a fixed pivot (shown in FIG. 27B), causing the lower gear 2705 to move in the opposing direction. The change in direction causes the connecting drive rod 2704 to automatically retract away from the patient, until the actuation lever reaches the end stops 2706 or the surgeon applies an opposing force on the actuation lever.

In accordance with some embodiments of the invention, the endoscope 200 can further comprise a suction control mechanism 240 coupled to the suction tube 220 and the actuator 230. The suction control mechanism 240 can connect the suction tube to a vacuum source when the suction tube 220 is extended and disconnect the suction tube 220 from the vacuum source when the suction tube 220 is retracted, e.g., fully retracted. The suction control mechanism 240 includes a suction valve 242 the moves within the manifold of the suction control mechanism 240 when the suction tube 220 is extended and retracted. Port 244 can be connected to a suction source (e.g., a source of vacuum such as a vacuum pump) In the Suction OFF position, the suction valve 242 is retracted and closed preventing suction from reaching the suction tube 220 as shown in FIG. 21C. In the Suction ON position, the suction valve 242 is extended and open allowing suction to reach the suction tube 220 as shown in FIG. 21D.

Figure 25A:
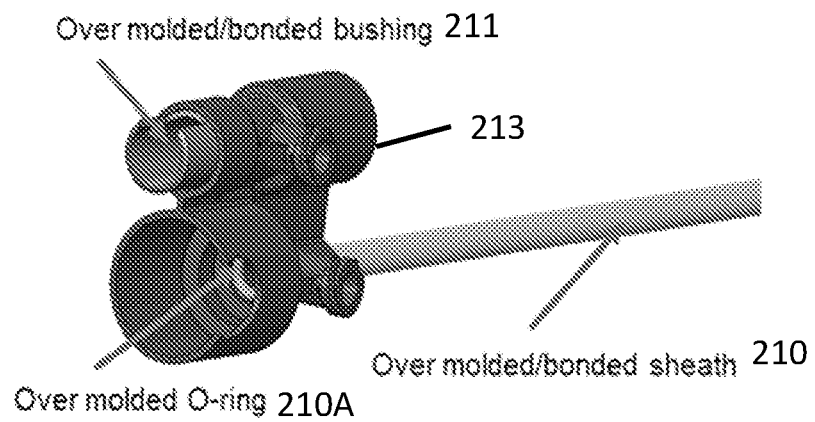
FIGS. 25A, 25B, 25C, 25D depict illustrations of component parts, that can be produced by, e.g., injection molding, 3D printing, machining, and/or multi-material casting.
Figure 25B:
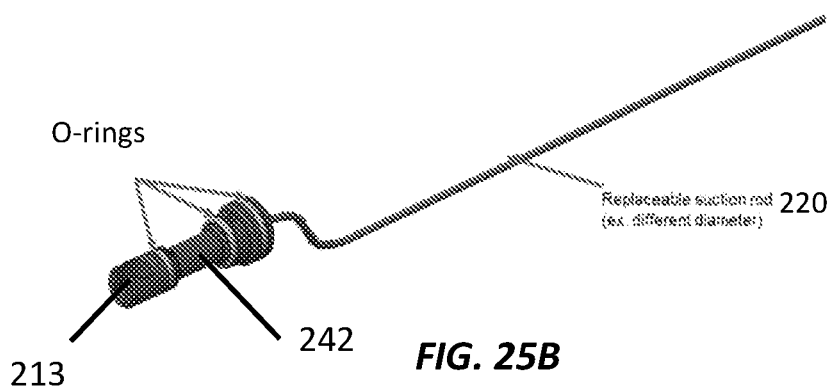

FIGS. 20A, 20B, 20C, 20D and FIGS. 21A, 21B, 21C, 21D depict one embodiment of a Suction/Irrigation assembly, which controls the delivery of the irrigation fluid as well as the actuation of the vacuum. An external irrigation pump can be turned ON or OFF when the user requires irrigation or cleansing fluid. In some embodiments, the external irrigation pump can be controlled by a foot pedal. When the pump is turned ON, the irrigation/cleansing fluid enters through the manifold port 2101 (FIG. 21A) and continues through the irrigation sheath 210 (FIG. 21B) which extends circumferentially around the tubular member of the endoscope 2010 forming an irrigation channel between the irrigation sheath 210 and the tubular member of the endoscope to transport irrigation fluid to the surgical site. An internal endoscope interface seal 210A (FIG. 21B and FIG. 25A) prevents the fluid from migrating back into the user's hand. In the case of the vacuum, an external vacuum device can be always ON. The vacuum can be configured such that it is shut off using the suction valve within the manifold 240 itself (FIG. 21C, "Suction OFF") when the suction tube is in the retracted position. When vacuum is desired, the user extends the suction tube 220 (FIG. 21B), which causes the suction valve (FIG. 21D, "Suction ON") to open and allow the vacuum to travel through the suction tube 220 and into the surgical site.

In some embodiments, a spacer block 2602 can be provided. The spacer block is an ergonomic attachment, e.g., to accommodate users with different size hands. One embodiment of the spacer block is depicted in FIG. 20A. For example, the thumb position necessary to actuate the safety button 230 (see FIG. 18) can be adjusted according to the size of the hand of the user. Users with larger hands also tend to have longer thumbs and thus the added spacer block can be used to position their hand further up or down and into a more comfortable position to apply the force to actuate the safety button.

In accordance with some embodiments of the invention, a foot pedal can be coupled to the external irrigation feed or the external vacuum pump. The foot pedal can turn the external irrigation feed or the external vacuum pump on or off.

In accordance with some embodiments of the invention, the connection of the suction tube 220 to a vacuum source can be controlled by a foot pedal. The foot pedal can be coupled to a valve or a suction pump. The foot pedal can control the valve or turn the suction pump on or off. For example, putting pressure on the foot pedal connects the suction tube 220 to the vacuum source (e.g., by opening the valve or turning the suction pump on) while removing pressure on the foot pedal disconnects the suction tube 220 from the vacuum source (e.g., by closing the valve or turning the suction pump off).

In accordance with some embodiments of the invention, the endoscopic system 200 can further comprise a separate irrigation tube (not shown) extending parallel to and alongside of the tubular member. The irrigation tube can be configured to direct a fluid from a fluid source to the distal end 214 of the endoscopic system 200. The separate irrigation tube can be coupled to the fluid source through a port. In accordance with some embodiments of the invention, the irrigation tube 210 can enclose the tubular member of the endoscope 202 such that the fluid flows between the inner surface of the irrigation tube 210 and the outer surface of the tubular member. In accordance with some embodiments of the invention, the irrigation tube 210 is on the outside of the tubular member but does not enclose the tubular member. In accordance with some embodiments of the invention, the irrigation tube is inside the tubular member, e.g., through the working channel of the endoscope. The distal end of the irrigation tube 210 can comprise one or more holes to facilitate the outward flow of the fluid. The fluid can be water, phosphate buffered saline, or any other fluids that are biocompatible. The fluid flow through the irrigation tube 210 can be actuated by a button or a foot pedal. The button or the foot pedal can be coupled to a valve or a fluid pump. The button or the foot pedal can control the valve or turn the fluid pump on or off.

In accordance with some embodiments of the invention, the irrigation tube 210 does not extend or retract. In accordance with some embodiments of the invention, the irrigation tube 210 can extend and retract. The mechanism for the extension and retraction of the irrigation tube can be similar to the ones used for the suction tube.

The irrigation fluid can be used to irrigate an area at the surgical site such that the endoscope's view is not obscured by solid or liquid debris. The irrigation fluid can be aspirated by the suction tube 220. In some embodiments, the irrigation fluid can rinse the endoscope lens, e.g., by forcing solid or liquid debris away from the lens.

Figure 3:
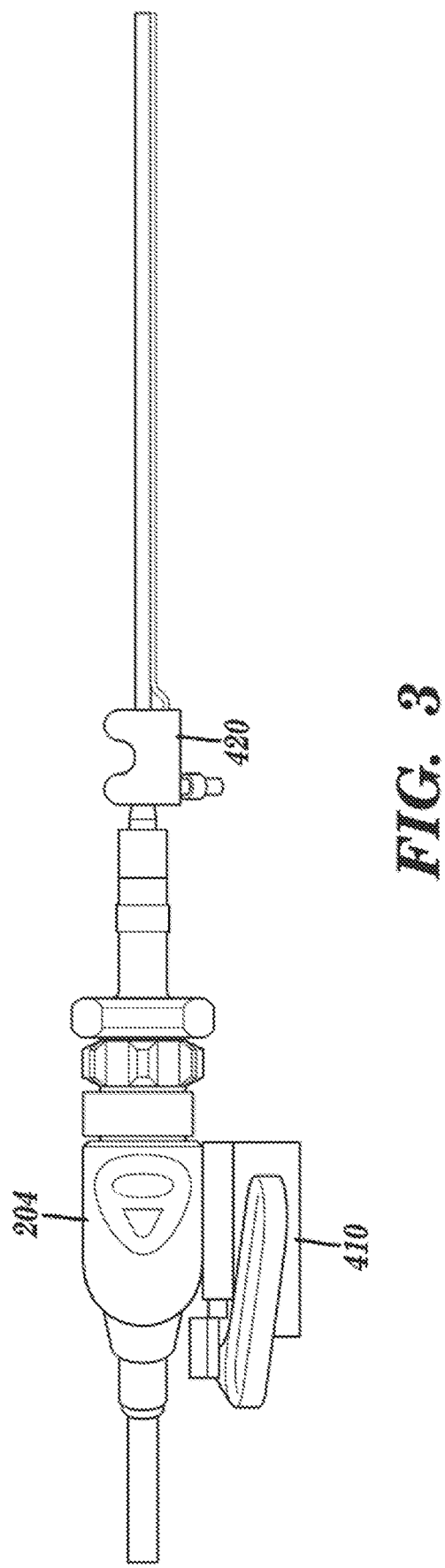
FIG. 3 is an illustration of an endoscope having an aspiration assembly attached thereon in accordance with some embodiments of the invention.

FIG. 3 is an illustration showing the top down view of the endoscope with the aspiration assembly attached thereon according to the invention.

Figure 4A:
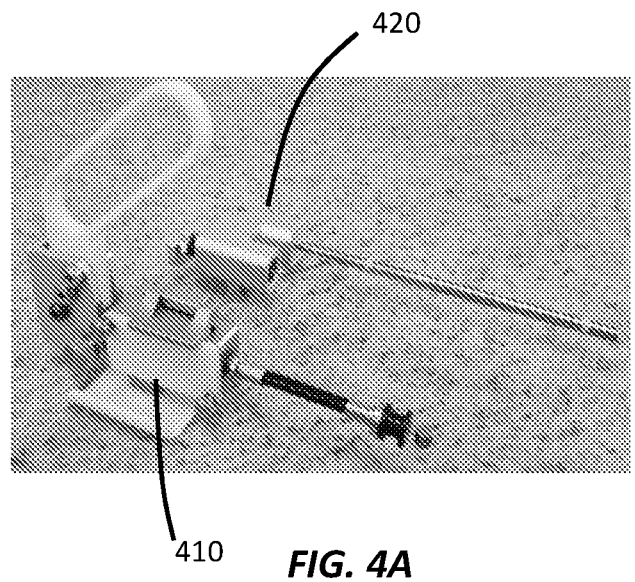
FIG. 4A is a photograph of the two sub-assemblies of the aspiration assembly in accordance with some embodiments of the invention. The two sub-assemblies are detached as shown in the photograph.
Figure 4B:
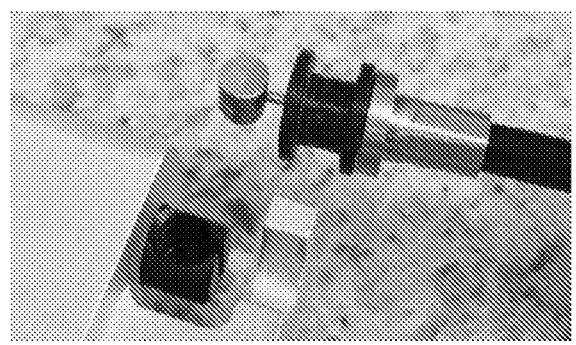
FIG. 4B is a photograph of the quick attachment system in accordance with some embodiments of the invention. The quick attachment system allows the actuator of the aspiration assembly to be coupled to the suction control mechanism of the aspiration assembly.
Figure 4C:
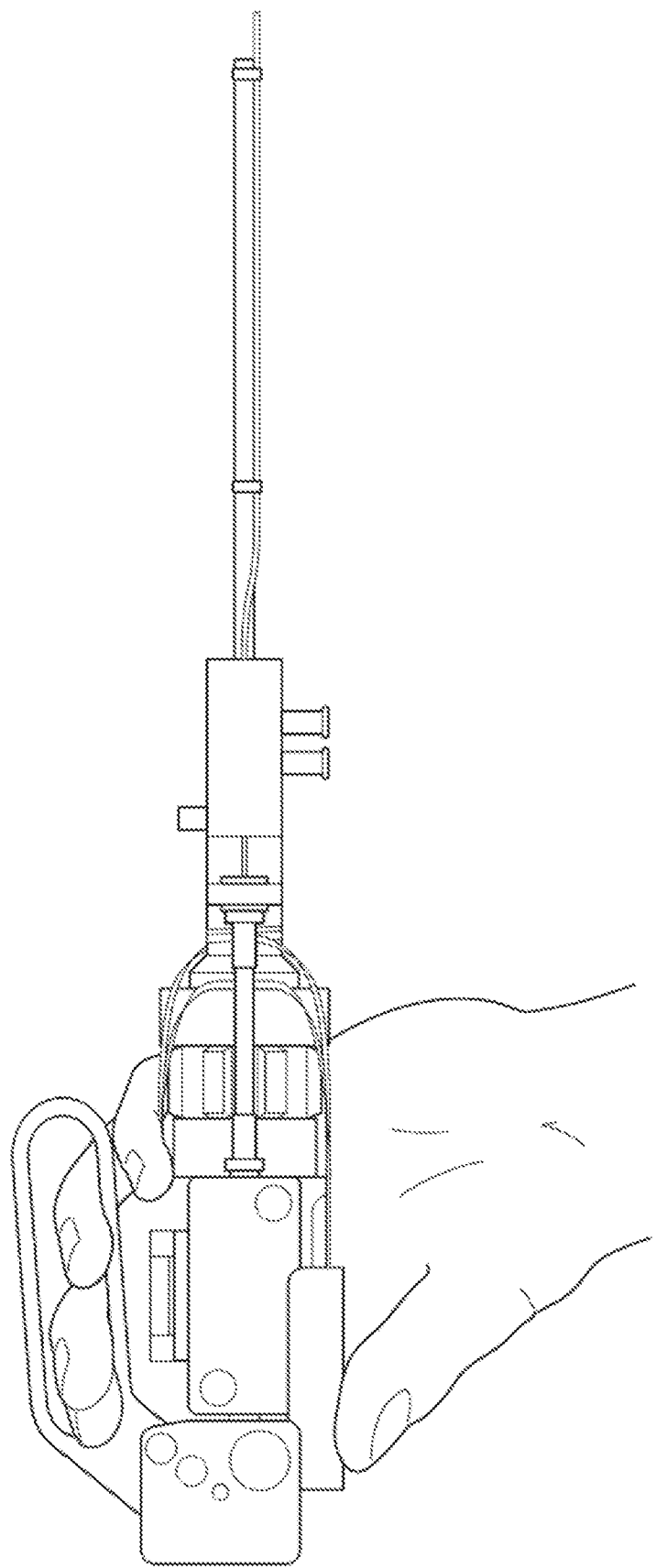
FIG. 4C is a photograph of the two sub-assemblies coupled together in accordance with some embodiments of the invention.

FIGS. 4A-4C are photographs showing the endoscopic system 200 with the aspiration assembly attached to the camera according to some embodiments of the invention. The aspiration assembly according to the invention can comprise two or more sub-assemblies that are detachable. For example, FIG. 4A shows a first sub-assembly 410 that comprises the actuator, and a second sub-assembly 420 that comprises the suction tube and the suction control mechanism. The first sub-assembly 410 can further comprise a push-pull cable or a pushrod adapted to be coupled to the second sub-assembly 420 as shown in FIG. 4B. FIG. 4C shows the first sub-assembly 410 mounted to the camera and the second sub-assembly 420 mounted on the sheath or the endoscope.

Some embodiments of the actuator according to the invention are shown in FIGS. 6-9 and FIGS. 10A-10C.

FIG. 6 is an illustration of an actuator 600 in accordance with some embodiments of the invention. The actuator 600 can comprise a set of gears such that a rotary handle motion can result in a linear motion of the suction tube. In accordance with some embodiments of the invention, the set of gears can comprise a first gear 610 on the handle, a second gear 612, and a gear rack 614. The first gear 610 can be coupled to the second gear 612 such that the rotary movement of the first gear 610 can result in the rotary movement of the second gear 612. The second gear 612 can be coupled to the gear rack 614 such that the rotary movement of the second gear 612 can result in the linear movement of the gear rack 614 which is coupled to the suction tube by a push-pull cable or pushrod thereby linearly moving the suction tube. As shown in FIG. 6, when the safety button 620 is not pressed, a leaf spring 634 forces two gear racks 640 to intermesh, locking the suction tube at a fixed position. A spring 630 can be preloaded to extend when the safety button 620 is pressed and no force applied to the handle portion 232, thereby retracting the suction tube. The spring 630 can also exert a force on a component of the suction control mechanism needed for the vacuum shut-off piston to create a seal. The spring 630 can also exert a force on a component of the suction control mechanism needed for the vacuum shut-off piston (not shown) to create a seal.

Some embodiments of the suction control mechanism according to the invention are shown in FIGS. 11A-11B and FIGS. 12, 13A, 13B.

As shown in FIGS. 11A and 11B, the suction control mechanism 1100 can comprise a chamber 1110 and a valve piston 1120 movable inside the chamber 1110 that can function as a suction valve selectively coupling the suction tube to a vacuum source. The valve piston 1120 can move inside the chamber 1110, e.g., along the axis parallel to the tubular member of the endoscope. In addition, the valve piston 1120 can comprise a channel 1122 coupled to a suction tube 1130, thereby permitting the suction tube 1130 to be connected to the gaseous environment of the chamber 1110. The suction control mechanism 1100 can be coupled to a vacuum source via a vacuum port 1140 and tubing. When the valve piston 1120 is at a resting state or fully retracted, the chamber 1110 and suction tube 1130 are disconnected from the vacuum source as shown in FIG. 11A. This can be done by sealing the chamber 1110 from the vacuum source. When the valve piston 1120 moves away from the vacuum port 1140 and thus extends the suction tube 1130, the chamber 1110 and suction tube 1130 are connected to the vacuum source as shown in FIG. 11B. The movement of the valve piston 1120 can be coupled to the movement of the movable handle as described in FIG. 6 by the push-pull cable or a pushrod.

Figure 14A:
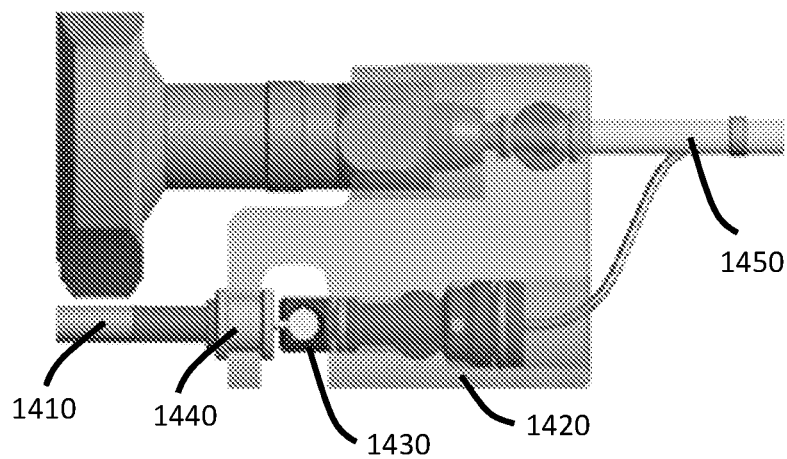
FIGS. 14A, 14B and 14C show illustrations of the push-pull cable that is detachable from the actuator in accordance with some embodiments of the invention.
Figure 14B:
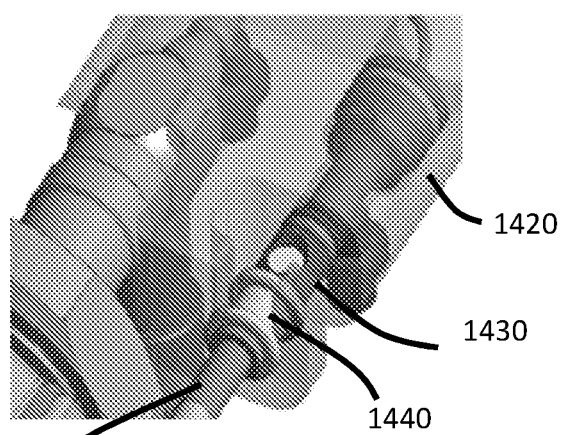
Figure 14C:
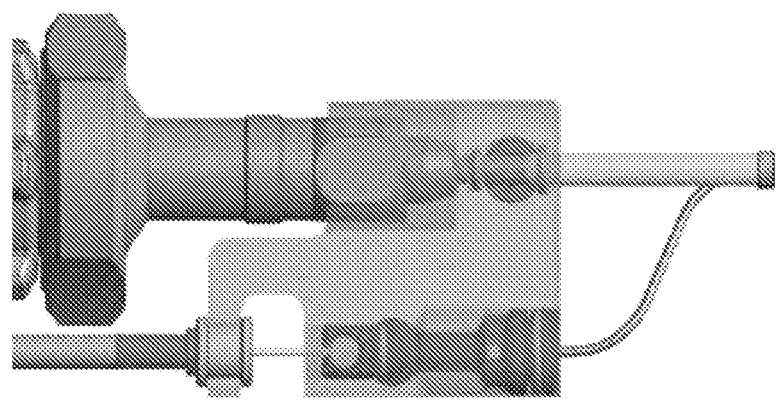

In accordance with some embodiments of the invention, the actuator can be adapted to be detachable from the suction tube or the suction control mechanism such as shown in FIG. 4A-4B and FIGS. 14A, 14B, 14C. FIGS. 14A, 14B, 14C show an embodiment of the push-pull cable 1410 and the suction control mechanism 1420. The suction control mechanism 1420 can comprise a slot 1430 for receiving one end of the push-pull cable 1410 comprising a retaining ring 1440.

Figure 15A:
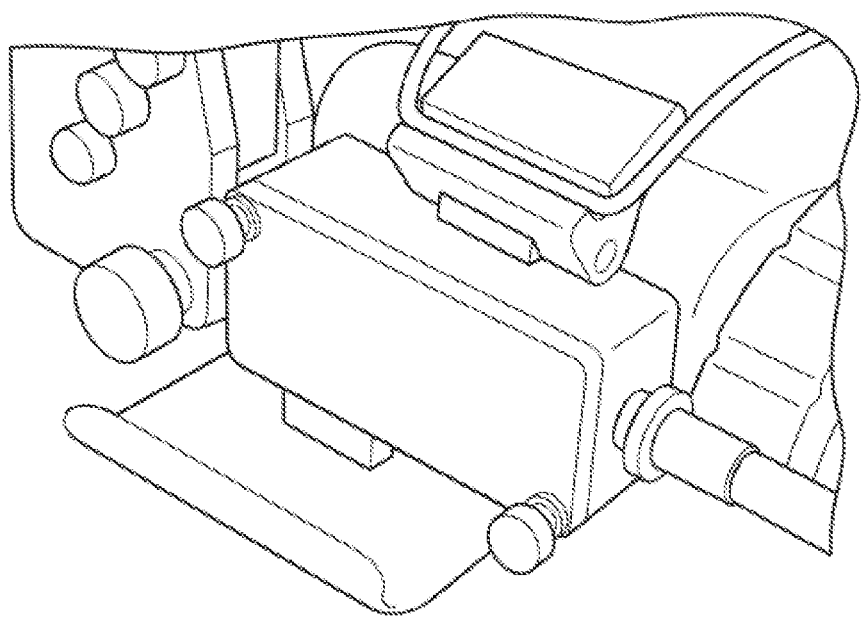
FIGS. 15A and 15B show a set of photographs showing the operation of the over-center locking system in accordance with some embodiments of the invention. The over-center locking system allows the aspiration assembly to be attached to the proximal end of the endoscope or to the camera coupled to the proximal end of the endoscope.
Figure 15B:
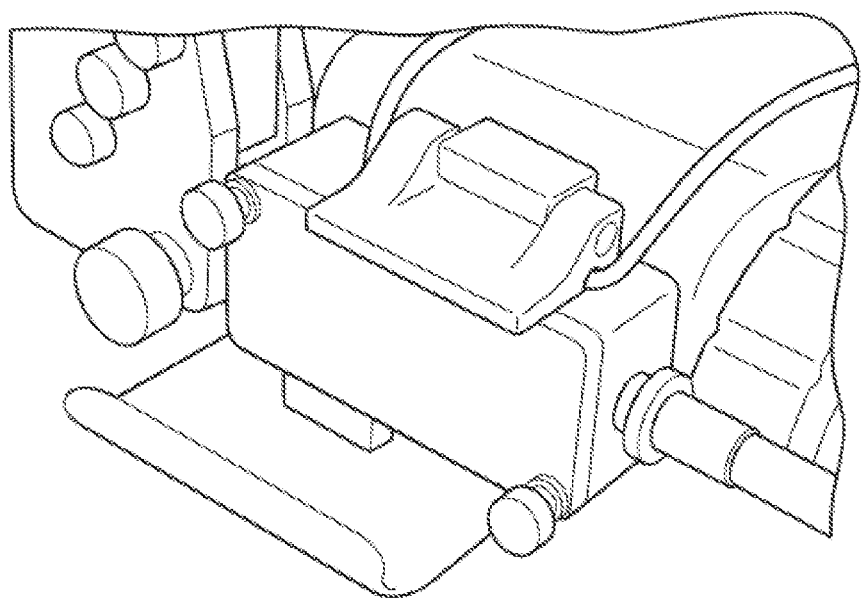
Figure 18:
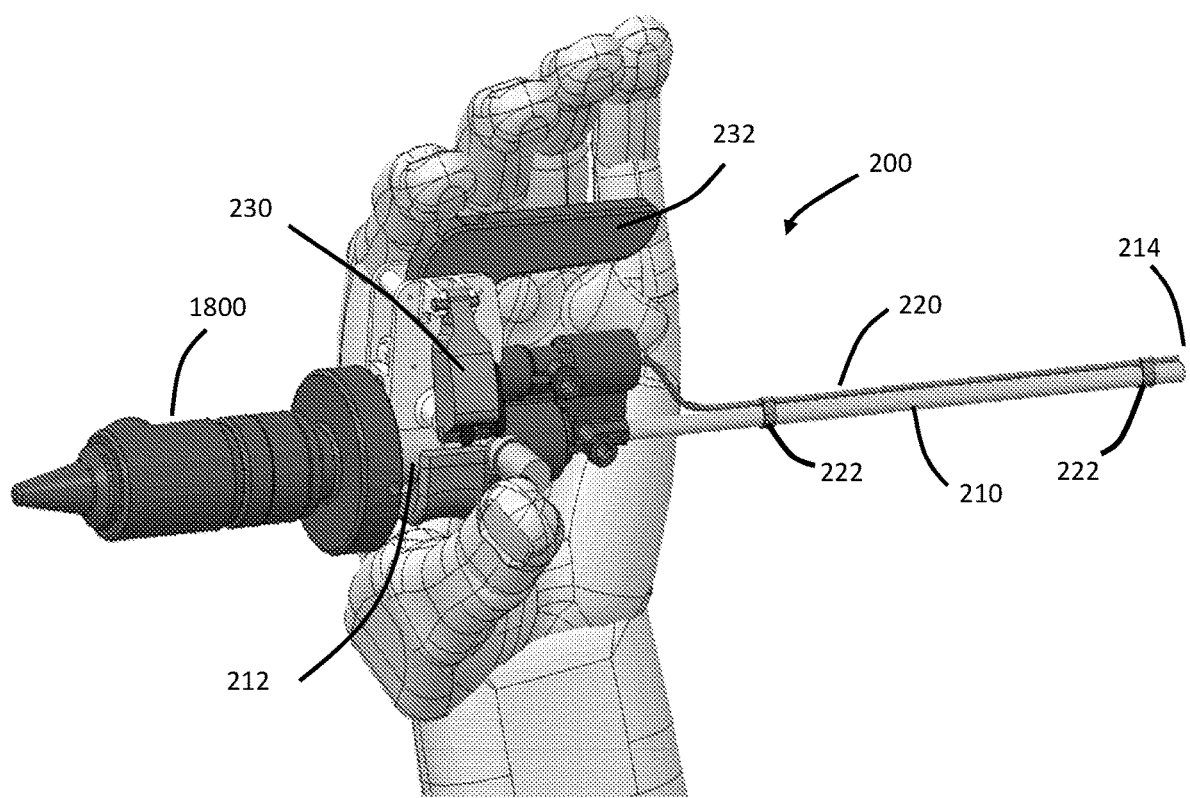
FIG. 18 is an illustration of one embodiment of the invention.
Figure 19A:
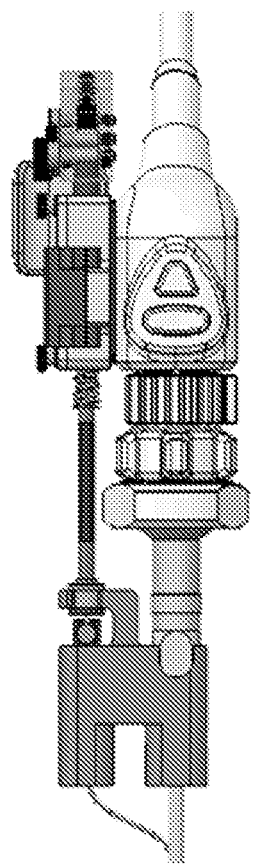
FIGS. 19A and 19B show illustrations of some embodiments of the invention with different endoscope cameras.
Figure 19B:
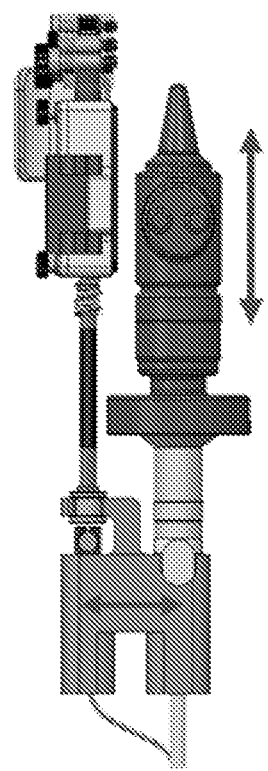
Figure 25C:
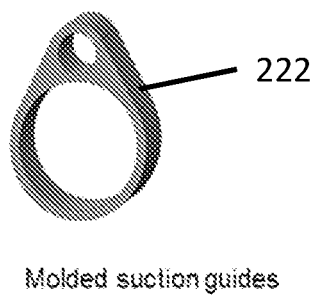
Figure 25D:
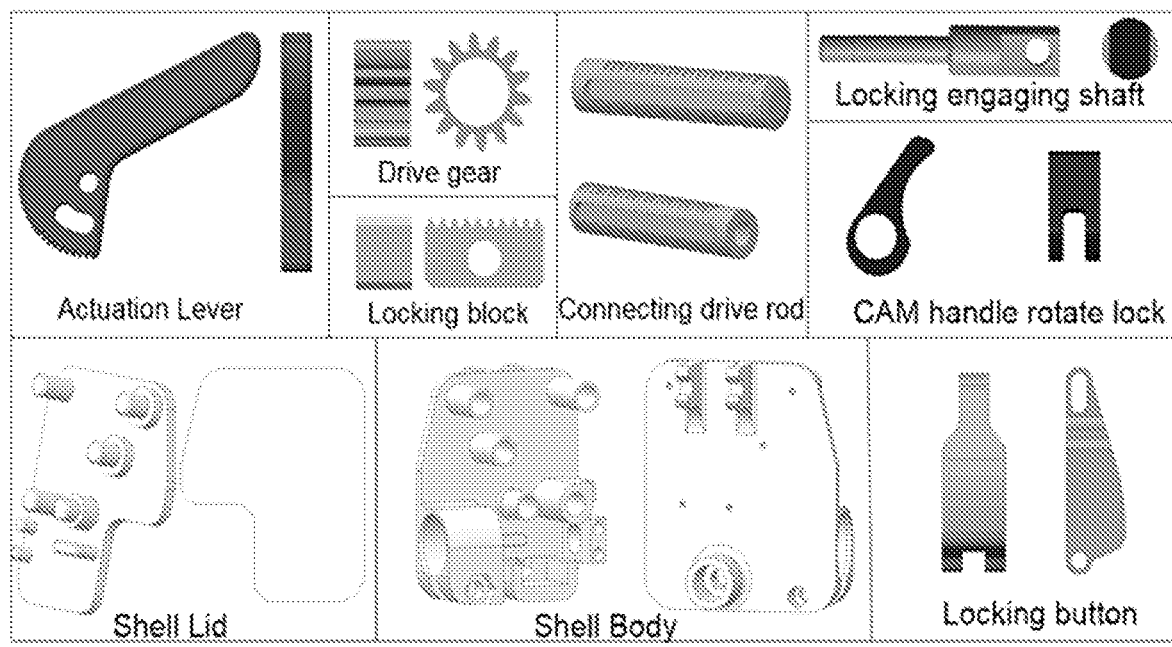
Figure 26A:
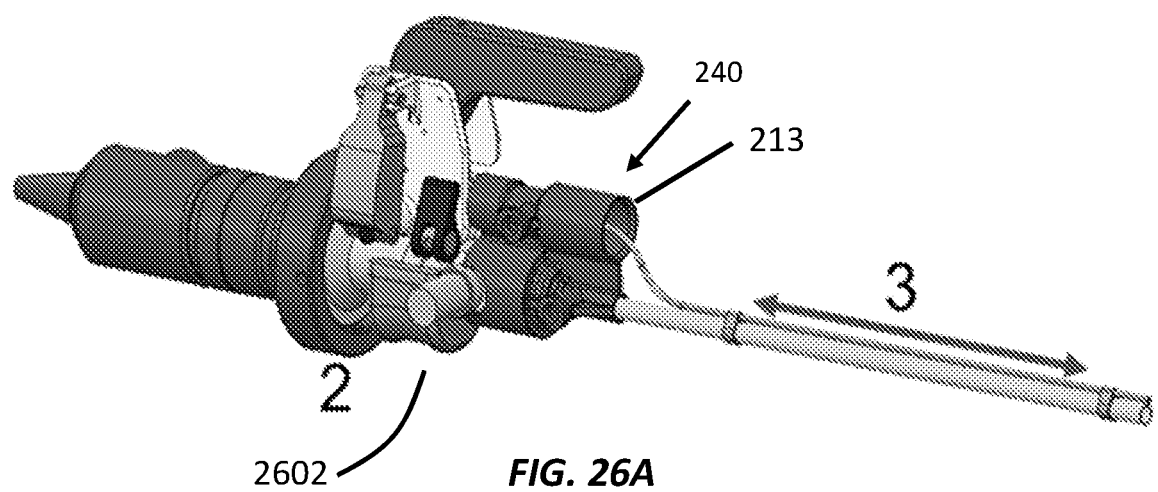
FIGS. 26A, 26B, 26C, 26D depict illustrations of aspects of embodiments of the invention where the camera attaches to the distal end of the endoscope. 1. The handle can be rotated with respect to the manifold to accommodate surgeon comfort. A cam clamp 2601 can be used to lock the actuator assembly in position. In the locked position, as shown in FIGS. 26A and 26C, the cam clamp locks the actuator assembly and the handle in a fixed angular position with respect to the endoscope. To unlock the cam clamp 2601, the cam clamp lever can be rotated "down" as indicated by the arrow in FIG. 26C. In the unlocked position, actuator assembly can be rotated around the bushing 211. A flexible portion 2603 in the actuator assembly wraps at least partially around the bushing 211 (e.g. in a semi-circle), with minimal clearance. When the cam clamp 1601 is in the locked position, the walls of the flexible portion are pulled closer together, creating a friction lock around the bushing 211.
Figure 26B:
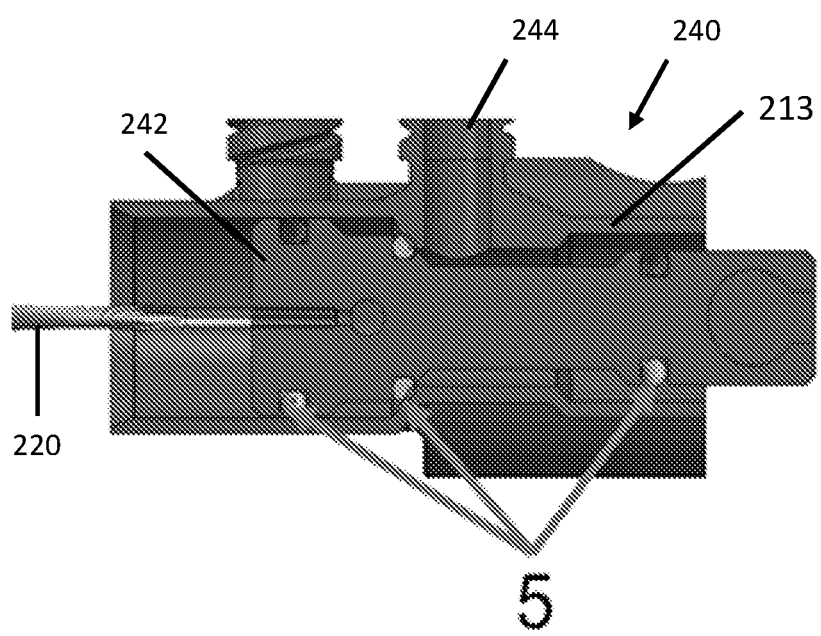
Figure 26C:
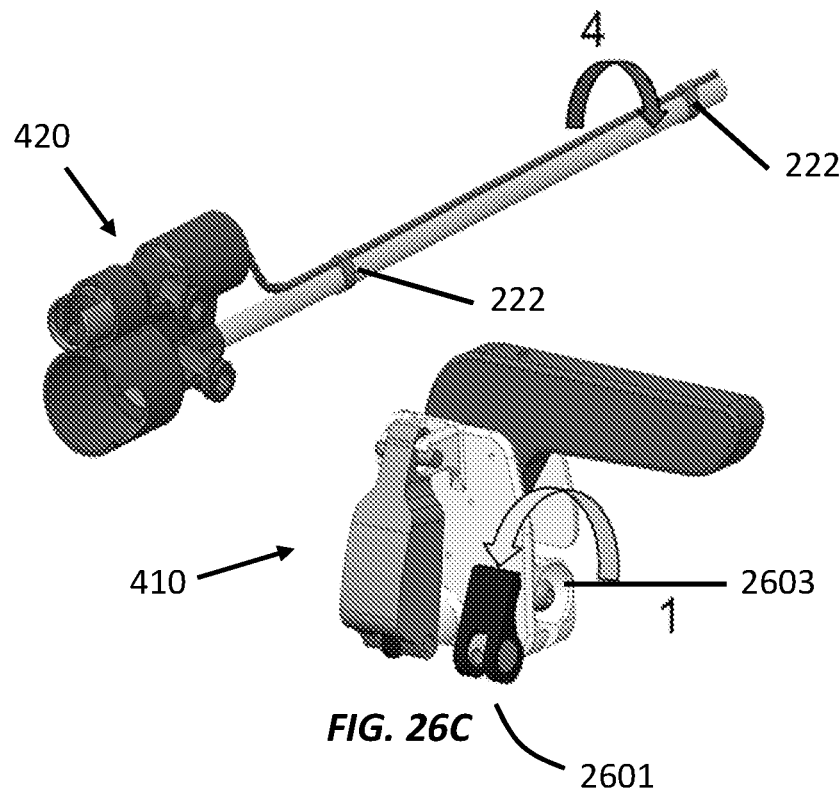
Figure 26D:
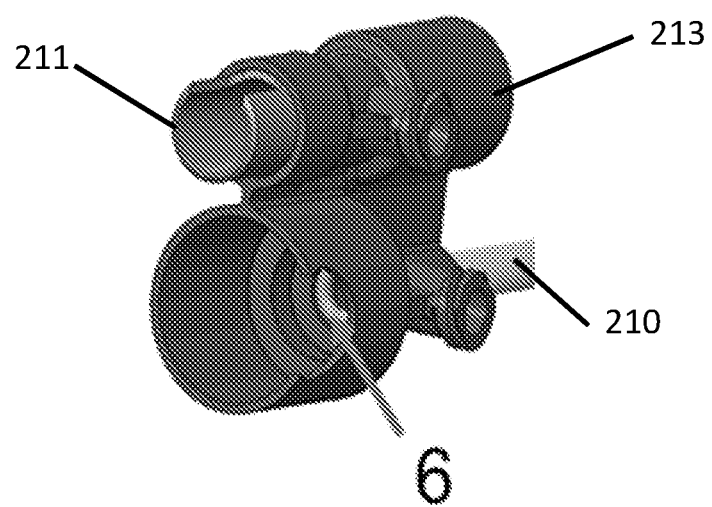

Attachment of the aspiration assembly onto an endoscope can be done in a variety of ways. In accordance with some embodiments of the invention, the actuator of the aspiration assembly can be attached to the camera at the proximal end of the endoscope through an over-center latching mechanism such as shown in FIGS. 15A and 15B or the proximal end of the endoscopic system by a slide-on or snap-on mechanism as shown in FIG. 18. The suction tube can be attached to the irrigation tube 220 (or the tubular member of the endoscope) through one or more latches that engage a cable that wraps around the endoscope or clips or guides 222 the slide over the irrigation tube 220 (or the tubular member) and provide guide holes for the suction tube as shown in FIGS. 21B, 25C, 26A. In the locked position, the latch of the over-center latching mechanism holds the cable tightly around the endoscope and the tension of the cable keeps the latch from opening.

The suction tube has an opening at a distal end of the suction tube adapted to remove smoke, or solid or liquid debris from surgery such as blood, an irrigation fluid, Cerebral Spinal fluid, transudate, exudate, mucous, a blood clot, bone fragments, or tissue fragments that can obscure the field of view. The distal end of the suction tube can be positioned in the field of view of the endoscope while the suction tube is at least partially extended, such that the user can observe the distal end such that the suction tube does not accidentally damage the surrounding tissue. In some embodiments, the distal end of the suction tube can be positioned in the field of view of the endoscope while the suction tube is fully extended. The amount of extension of the suction tube can be no more than 2 inches, no more than 1.5 inches, no more than 1 inch, no more than 0.9 inch, no more than 0.8 inch, no more than 0.7 inch, no more than 0.6 inch, no more than 0.5 inch, or no more than 0.4 inch.

In accordance with some embodiments of the invention, a portion of the aspiration assemblies described herein can be disposable. For example, the suction tube and/or the actuator can be disposable.

The aspiration assemblies described herein can be attached to either rigid or flexible endoscopes. The aspiration assemblies and endoscopes comprising the same can be manufactured using methods known to those skilled in the art. Exemplary methods include, but are not limited to, machining, extruding, casting, 3D printing, or any combinations thereof The endoscopes described herein can be operated single-handedly and used in a variety of endoscopic procedures. In accordance with some embodiments of the invention, the endoscopes described herein can be used in laparoscopic surgery. In accordance with some embodiments of the invention, the endoscopes described herein can be used in arthroscopic surgery. The dimensions and features of the endoscopes can depend on the type of endoscopic surgery being performed.

The present invention can use many different configurations of the visualization system that enable the user see images of the field of view from the distal end of the endoscopic system 200. In accordance with some embodiments, the visualization system can include one or more lenses positioned along the length of the tubular member of the endoscope from the distal end 214 to the proximal end 212 that transmit images to an eye piece and/or camera mounted to the proximal end 212 of the endoscope. The visualization system can also include a light guide, such as a fiber optic light guide, that transmits illuminating light from the proximal end 212 to the distal end 214 of the endoscope to illuminate the field of view. The light guide can include optical fibers and or lenses positioned along the length of the tubular member of the endoscope from the distal end 214 to the proximal end 212 that transmits light to the distal end 214. In accordance with some embodiments, the endoscope can include optical fibers that transmit images of the field view to eye piece and/or camera at the proximal end 212. In accordance with some embodiments, the visualization system can include a camera mounted at the distal end 214 of the endoscope that transmits (e.g., by wire or wirelessly) images of the field of view to the proximal end 212 and/or to a presentation display for the user to view. In accordance with some embodiments, one or more illumination elements, such as Light Emitting Diodes (LEDs) can be mounted at the distal end of the endoscope to provide illumination instead of or in addition to the light guide.

FIG. 18 shows an endoscopic system 200 in accordance with some embodiments of the invention. The endoscopic system 200 can comprise a tubular member of an endoscope that is encircled by a sheath 210, which defines an irrigation channel between the inner surface of the sheath 210 and the outer surface of the tubular member of the endoscope that extends from the proximal end 212 to the distal end 214 of the endoscopic system 200, and a camera 1800 coupled to the proximal end 212 of the endoscope and adapted to provide images of the field of view from the distal end 214 to a display screen for the user. The endoscopic system 200 can further include an extendable suction tube 220 extending along the sheath 210, the suction tube 220 being able to extend or retract relative to the distal end 214. The length of the suction tube 220 can be similar in length to the sheath 210. The suction tube 220 can be connected through a valve to a vacuum source such that the suction tube 220 is connected to the vacuum source when the suction tube 220 is extended and disconnected from the vacuum source when the suction tube 220 is retracted.

Figure 23:
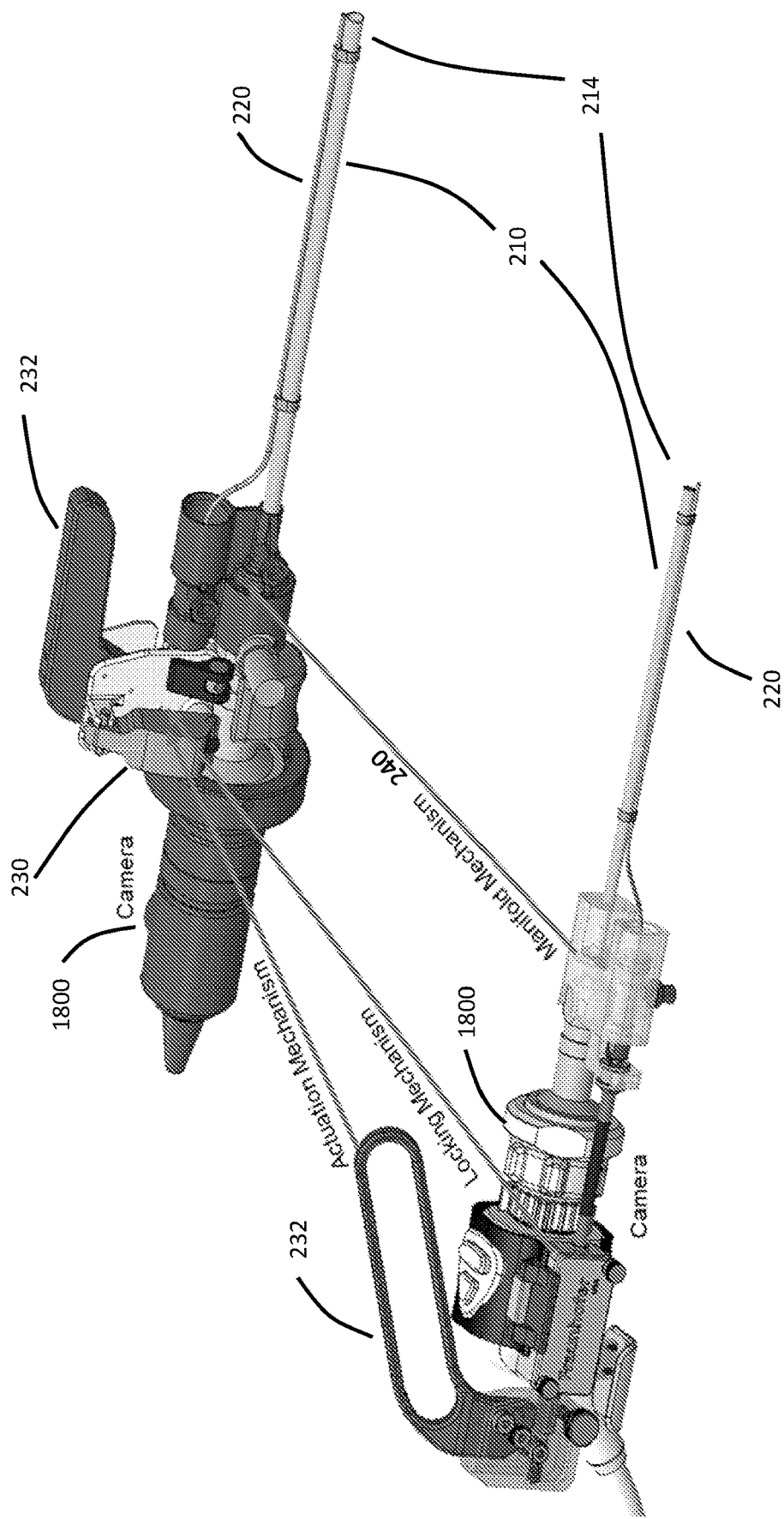
FIG. 23 depicts an illustration of two embodiments of the endoscopic aspiration systems described herein.
Figure 24A:
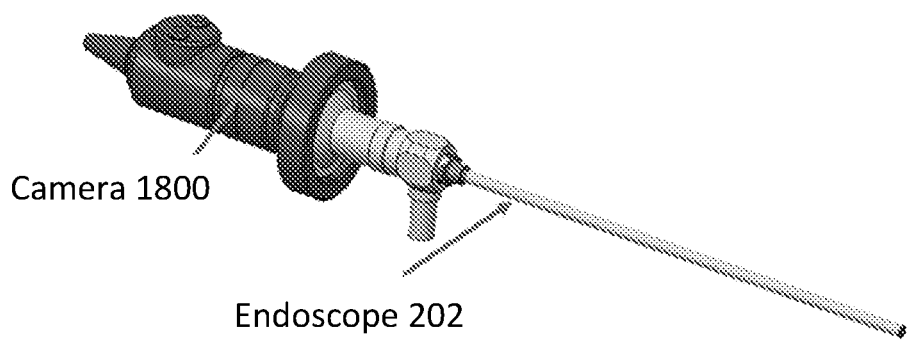
FIGS. 24A and 24B depict illustrations of embodiments of the endoscopic aspiration systems described herein wherein the camera is attached via the distal end of the endoscope.
Figure 24B:
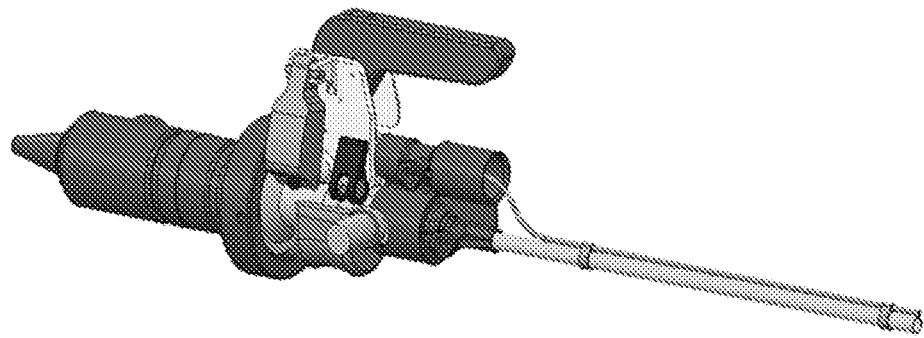

As depicted in FIGS. 18 and 23, and in accordance with any of the embodiments of the invention, the camera 1800 can be coupled to the proximal end 212 of the endoscopic system 200 and the actuator 230 (which can optionally include the locking mechanism) can be coupled to the sheath 210 (or the camera 1800 or to the endoscope) either directly, or to the suction control mechanism 240 (e.g., manifold mechanism and suction valve) which can be mounted on the sheath 210 as illustrated in FIG. 23. In accordance with any of the embodiments of the invention, the camera 1800 can be coupled to the proximal end 212 of the endoscopic system 200; the actuator 230 (which can optionally include the locking mechanism) can be coupled to the camera 1800 or to the endoscope, via the suction control mechanism 240 (e.g., manifold mechanism) mounted to the sheath 210; and the actuator 230 can be located parallel to and/or distal to the visualization system 1800, as illustrated in FIG. 23. In some configurations, the actuator 230 and locking mechanism can be coupled to the sheath 210 or the endoscope in order to permit the use of any camera 1800 design without having to adapt the actuator 230 and locking mechanism to be coupled to the housing of the camera 1800. This configuration is more readily adaptable for use with different cameras 1800 as camera body length and width can vary from model to model and make coupling of the actuator 230 and locking mechanism difficult. Such configurations eliminate the need for an insert or adaptor to fit smaller cameras into the system, permitting users to take advantage of the lighter weight and increased maneuverability of smaller cameras 1800. Finally, configurations in which the actuator 230 and locking mechanism are not coupled to the camera 1800 avoid bending of the cable assembly that can occur when a smaller diameter camera changes the spacing between the endoscope and the vacuum piston channel.

Figure 22A:
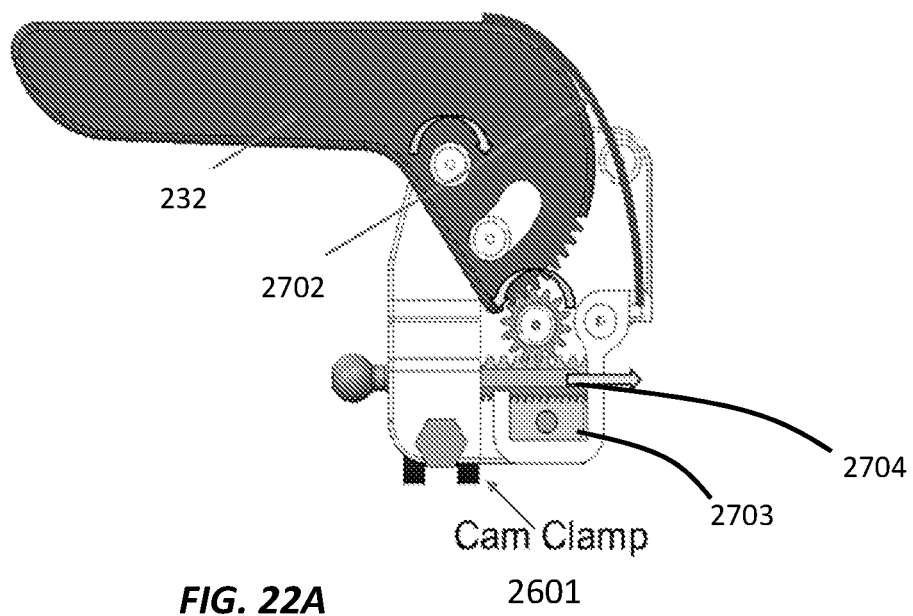
FIGS. 22A and 22B depict illustrations of the internal actuation (FIG. 22A) and locking elements (FIG. 22B) of certain embodiments described herein.
Figure 22B:
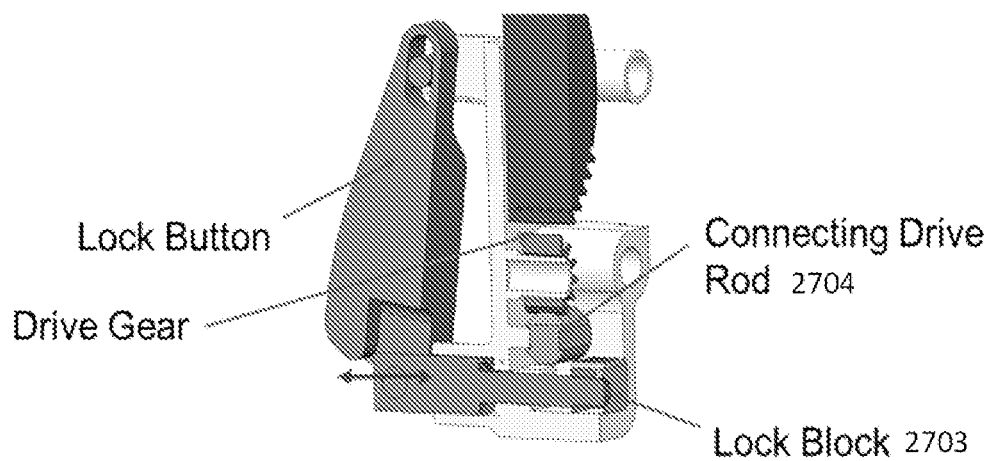

In accordance with any of the embodiments of the invention, the actuator 230 and locking mechanism can be combined into one assembly, e.g., as illustrated in FIGS. 22A and 22B and FIG. 23.

In accordance with any of the embodiments of the invention and as depicted in FIGS. 20B, 22A, 24B, 25A and 25B, and 27A and 27B, the actuator 230 and the suction control mechanism 240 (e.g., manifold mechanism) can attach to each other using a pivot joint and cam lock. In some embodiments, the endoscope 202 (with or without camera 1800 attached) can be inserted into the bottom channel of the suction/irrigation housing 213 (FIG. 25A) through the O-ring seal 210A (e.g., snap-fit or press-fit in place) and using the semicircle shaped feature or bushing 211 on the manifold 240, the actuator assembly 230 can be mounted to suction control mechanism 240. The actuator assembly 230 can include a ball 2704A on the gear rack 2704 that can engage a slot 242A in suction valve 242 of the manifold 240 forming a pivot joint that enables motion of the gear rack 2704 to move suction valve 242 of the manifold 240 and the suction tube 220 along the endoscope as shown in FIG. 21B.

The parts of the endoscopic aspiration systems described herein can be produced, e.g., by injection molding and/or multi-material molding. FIG. 25 depicts parts that can be produced by such methods.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are described herein.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the term "comprising" or "comprises" is used in reference to compositions, methods, and respective component(s) thereof, that are useful to an embodiment, yet open to the inclusion of unspecified elements, whether useful or not.

As used herein, the term "consisting essentially of" refers to those elements for a given embodiment. The term permits the presence of elements that do not materially affect the basic and novel or functional characteristic(s) of that embodiment of the invention.

Other than in the operating examples, or where otherwise indicated, all numbers expressing quantities of ingredients or reaction conditions used herein should be understood as modified in all instances by the term "about." The term "about" when used in connection with percentages may mean ±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. An endoscope comprising:
   a tubular member extending from a proximal end to a distal end; the tubular member including a visualization system configured to transmit images a field of view from the distal end of the tubular member to the proximal end of the tubular member;
   an extendable suction tube coupled to the tubular member and adapted to move axially beyond the distal end of the tubular member; and an actuator coupled to the suction tube to extend or retract the suction tube with respect to the distal end of the endoscope when the actuator is actuated.

2. The endoscope of paragraph 1, wherein the suction tube is connected to a vacuum source when the suction tube is extended and the suction tube is disconnected from the vacuum source when the suction tube is retracted.

3. The endoscope of paragraph 1, wherein the suction tube has an opening at a distal end of the suction tube to aspirate smoke, or solid or liquid debris selected from the group consisting of blood, an irrigation fluid, cerebral spinal fluid, transudate, exudate, mucous, a blood clot, a bone fragment, and a tissue fragment.

4. The endoscope of paragraph 1, wherein the distal end of the suction tube is in the field of view of the endoscope when the suction tube is at least partially extended.

5. The endoscope of paragraph 1, wherein the actuator comprises a handle portion coupled to the suction tube and configured to extend or retract the suction tube.

6. The endoscope of paragraph 5, wherein the handle portion comprises a movable handle configured to extend or retract the suction tube when the movable handle is actuated.

7. The endoscope of paragraph 6, wherein the actuator comprises a first gear coupled to a second gear of the movable handle, and a gear rack coupled to the first gear, thereby converting a rotary handle motion to a linear motion of the suction tube.

8. The endoscope of paragraph 1, wherein the actuator comprises a locking mechanism configured to lock the suction tube at a fixed position.

9. The endoscope of paragraph 8, wherein the locking mechanism comprises a pair of gear racks configured to intermesh to lock the suction tube at a fixed position.

10. The endoscope of paragraph 8, wherein the actuator comprises a safety button coupled to the locking mechanism and configured to unlock the locking mechanism when the safety button is actuated, thereby permitting the movement of the suction tube away from the patient.

11. The endoscope of paragraph 5, wherein the actuator further comprises a push-pull element coupled to the handle portion and the suction tube, whereby the handle portion actuates the push-pull element to extend or retract the suction tube.

12. The endoscope of paragraph 1, wherein the actuator is coupled to the suction tube through a suction control mechanism.

13. The endoscope of paragraph 12, wherein the actuator is adapted to be detachable from the suction control mechanism.

14. The endoscope of paragraph 12, wherein the suction control mechanism comprises a piston coupled to the vacuum source and the suction tube.

15. The endoscope of paragraph 1, wherein the suction tube is attached to the tubular member through one or more guide clips.

16. The endoscope of paragraph 15 wherein one or more of the guide clips are rotatable around the tubular member to enable the suction tube to move circumferentially around the tubular member.

17. The endoscope of paragraph 1, wherein the actuator is attached at the proximal end of the endoscope through an over-center latching mechanism.

18. The endoscope of paragraph 1, further comprising an irrigation tube extending along the tubular member and configured to direct a fluid from a fluid source to the proximity of the distal end of the endoscope.

19. The endoscope of paragraph 18, wherein the irrigation tube encloses the tubular member, whereby the fluid flows on the outside of the tubular member.

20. The endoscope of paragraph 18, wherein the irrigation tube is inside the tubular member.

21. The endoscope of paragraph 1, wherein the tubular member is rigid.

22. The endoscope of paragraph 1, wherein the suction tube is connected to a vacuum source.

23. The endoscope of paragraph 1, wherein the actuator comprises a motor.

24. The endoscope of paragraph 1, wherein the actuator comprises a pneumatic actuator.

25. The endoscope of paragraph 1, wherein the actuator comprises a hydraulic actuator.

26. The endoscope of paragraph 1, wherein the actuator comprises a spring.

27. An aspiration assembly for attaching to an endoscope, wherein the endoscope comprises a working channel extending through a tubular member from a proximal end to a distal end of the endoscope and a visualization system coupled to the distal end and adapted to provide images from a field of view at the distal end to the proximal end of the endoscope, the aspiration assembly comprising:
 an extendable suction tube configured to couple to the tubular member and move axially beyond the distal end of the tubular member; and
 an actuator configured to couple to the suction tube and extend or retract the suction tube with respect to the distal end of the endoscope when the actuator is actuated.

28. The aspiration assembly of paragraph 27, wherein the suction tube is connected to a vacuum source when the suction tube is extended and the suction tube is disconnected from the vacuum source when the suction tube is retracted.

29. The aspiration assembly of paragraph 27, wherein the suction tube has an opening at a distal end of the suction tube adapted to aspirate smoke, or solid or liquid debris selected from the group consisting of blood, an irrigation fluid, a blood clot, a bone fragment, and a tissue fragment.

30. The aspiration assembly of paragraph 29, wherein the distal end of the suction tube is positioned to be in the field of view of the endoscope when the suction tube is at least partially extended.

31. The aspiration assembly of paragraph 27, wherein the actuator comprises a handle portion coupled to the suction tube and configured to extend or retract the suction tube.

32. The aspiration assembly of paragraph 31, wherein the handle portion comprises a movable handle configured to extend or retract the suction tube when the movable handle is actuated.

33. The aspiration assembly of paragraph 32, wherein the actuator comprises a first gear coupled to a second gear of the movable handle, and a gear rack coupled to the first gear, thereby converting a rotary handle motion to a linear motion of the suction tube.

34. The aspiration assembly of paragraph 27, wherein the actuator comprises a locking mechanism configured to lock the suction tube at a fixed position.

35. The aspiration assembly of paragraph 34, wherein the locking mechanism comprises a pair of gear racks configured to intermesh to lock the suction tube at a fixed position.

36. The aspiration assembly of paragraph 34, wherein the actuator comprises a safety button coupled to the locking mechanism and configured to unlock the locking mechanism when the safety button is actuated, thereby permitting the movement of the suction tube.

37. The aspiration assembly of paragraph 31, wherein the actuator further comprises a push-pull element coupled to the handle portion and the suction tube, whereby the handle portion actuates the push-pull element to extend or retract the suction tube.

38. The aspiration assembly of paragraph 27, wherein the actuator is coupled to the suction tube through a suction control mechanism.

39. The aspiration assembly of paragraph 38, wherein the actuator is adapted to be detachable from the suction control mechanism.

40. The aspiration assembly of paragraph 38, wherein the suction control mechanism comprises a piston coupled to the vacuum source and the suction tube.

41. The aspiration assembly of paragraph 27, wherein the suction tube is attached to the tubular member through one or more guide clips.

42. The aspiration assembly of paragraph 31, wherein the handle portion is attached at the proximal end of the endoscope through an over-center latching mechanism.

43. The aspiration assembly of paragraph 27, further comprising an irrigation tube extending along the tubular member and configured to direct a fluid from a fluid source to the proximity of the distal end of the endoscope.

44. The aspiration assembly of paragraph 43, wherein the irrigation tube encloses the tubular member, whereby the fluid flows on the outside of the tubular member.

45. The aspiration assembly of paragraph 43, wherein the irrigation tube is inside the tubular member.

46. The aspiration assembly of paragraph 27, wherein the tubular member is rigid.

47. A method of removing an object inside a body, the method comprising:
   (i) attaching an aspiration assembly of paragraph 27 to an endoscope;
   (ii) coupling the aspiration assembly to a vacuum source;
   (iii) inserting the endoscope into the body; and
   (iv) extending the distal end of the suction tube of the aspiration assembly to the vicinity of the object to draw the object into the suction tube.

48. The method of paragraph 47, wherein the object is smoke, or solid or liquid debris selected from the group consisting of blood, an irrigation fluid, cerebral spinal fluid, transudate, exudate, mucous, a blood clot, a bone fragment, and a tissue fragment.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1

Development of an Aspiration Assembly for Attaching to an Endoscope

Surgical Device Design

When developing a surgical device, several design aspects should be taken into account.

Sterilization. All surgical devices must undergo sterilization before they can be used on a patient. Sterilization is a process that removes or kills all forms of life and thus ensures no transmissible agents such as bacteria and viruses can be transmitted from the device to patient. Sterilization techniques may apply heat, chemicals, radiation, irrigation, high pressure or a combination thereof to eliminate all contaminations. Many different sterilization techniques exist. The most commonly used method in hospitals is autoclaving. Autoclaves use heat, steam and pressure, or dry heat and pressure to kill all life in a sealed chamber.

Ethylene oxide (ETO) is also a commonly used technique that uses the chemical ethylene-oxide. This method is more costly but doesn't require heat and thus is often used for materials that aren't resistant to high temperatures. A common and cost-effective sterilization method is autoclave. The method of sterilization affects the materials that can be used, and can also add design requirements. For example, a long thin tube cannot be sterilized by ETO as the gasses will not reach all the way into the tube, in this case the tube has to be made disposable or detachable from the device so that it can undergo a different sterilization method.

Materials for Surgical Devices. In addition to the sterilization method, medical standards also affect the materials than can be used. In general, materials used in medical devices may not interact or react with the human body. The materials also may not contain any impurities that may excrete over time and need to be highly corrosion resistant since they may be exposed to corrosive environments. The exact requirements and standards depend on the type of device. For example, surgical tools, dental tools and temporary implanted fixture devices are often made from austenitic stainless steels (e.g. 300 series) as these are relatively inexpensive. However, these austenitic stainless steels are not sufficiently corrosion resistant for long-term implantation.

Ergonomics for One Handed Use. It is desirable that the user is able to manipulate surgical devices carefully and precisely, sometimes in awkward orientations and for extended periods of time. A poor ergonomic design can cause fatigue, discomfort or reduced accuracy, in the worst case this will negatively affect surgical outcome. In some endoscopic surgery, one hand can be used to hold the endoscope, and the other can be used to manipulate the tools.

Ergonomic Embodiments

Figure 7:
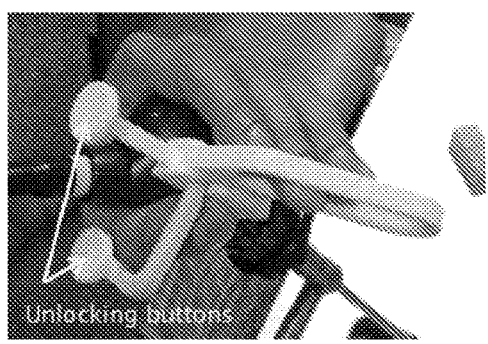
FIG. 7 is a photograph of an actuator attached to an endoscope according to the invention.
Figure 8:
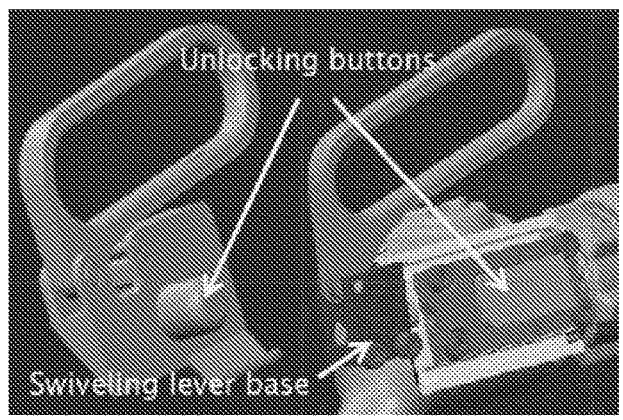
FIG. 8 illustrates two embodiments of the actuator according to the invention. For the embodiment on the left, the actuator has one unlocking button on the side and the lever had been brought from 45 to a 15 degree angle. For the embodiment on the right, the lever was placed on a swiveling base that can be adjusted for different hand sizes. The swiveling lever base allows adjustment of the angle, accommodating both small and large hands.
Figure 16A:
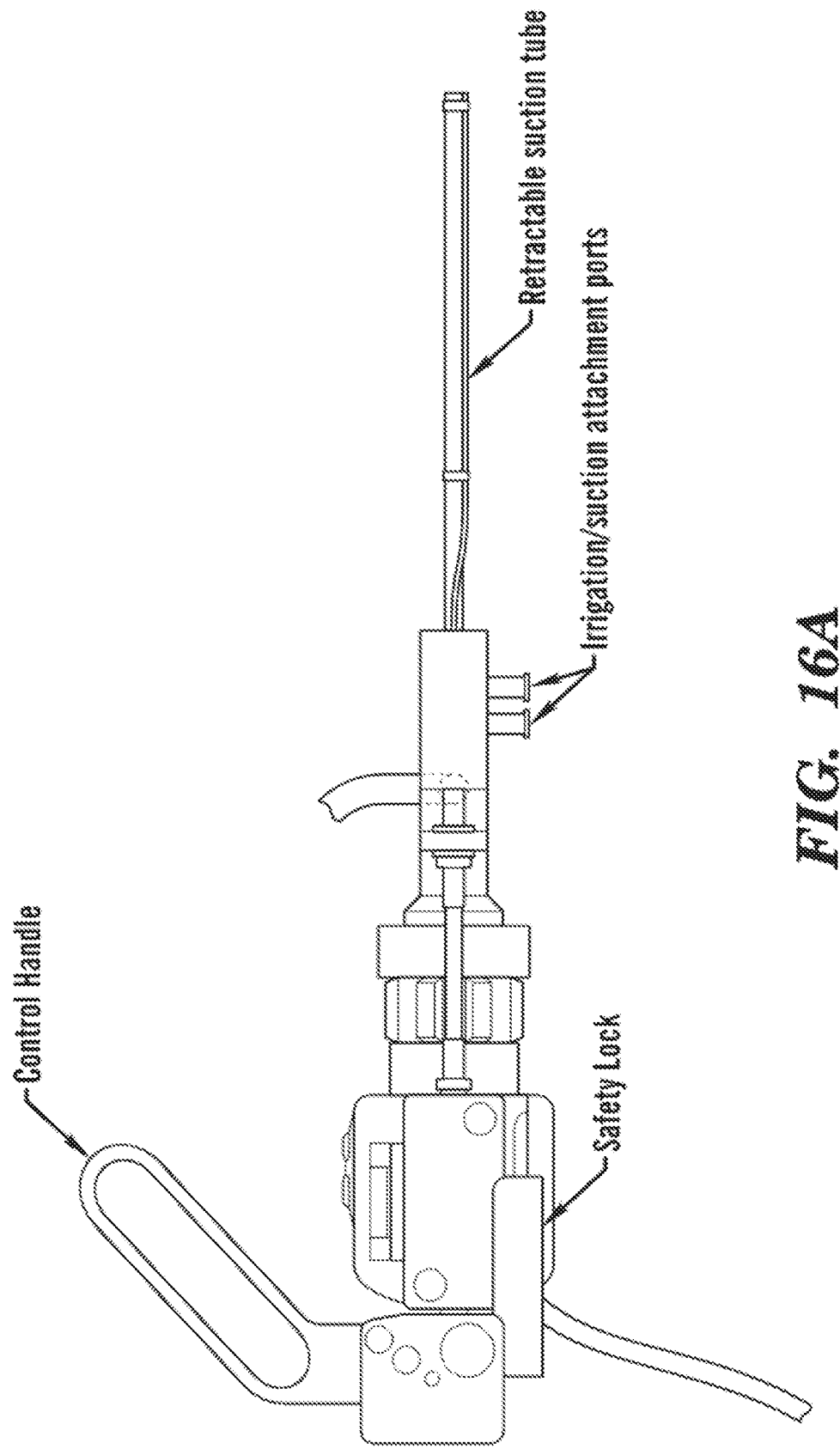
FIGS. 16A-16D are photographs and schematics showing an endoscope having an aspiration assembly attached thereon in accordance with some embodiments of the invention.
Figure 16B:
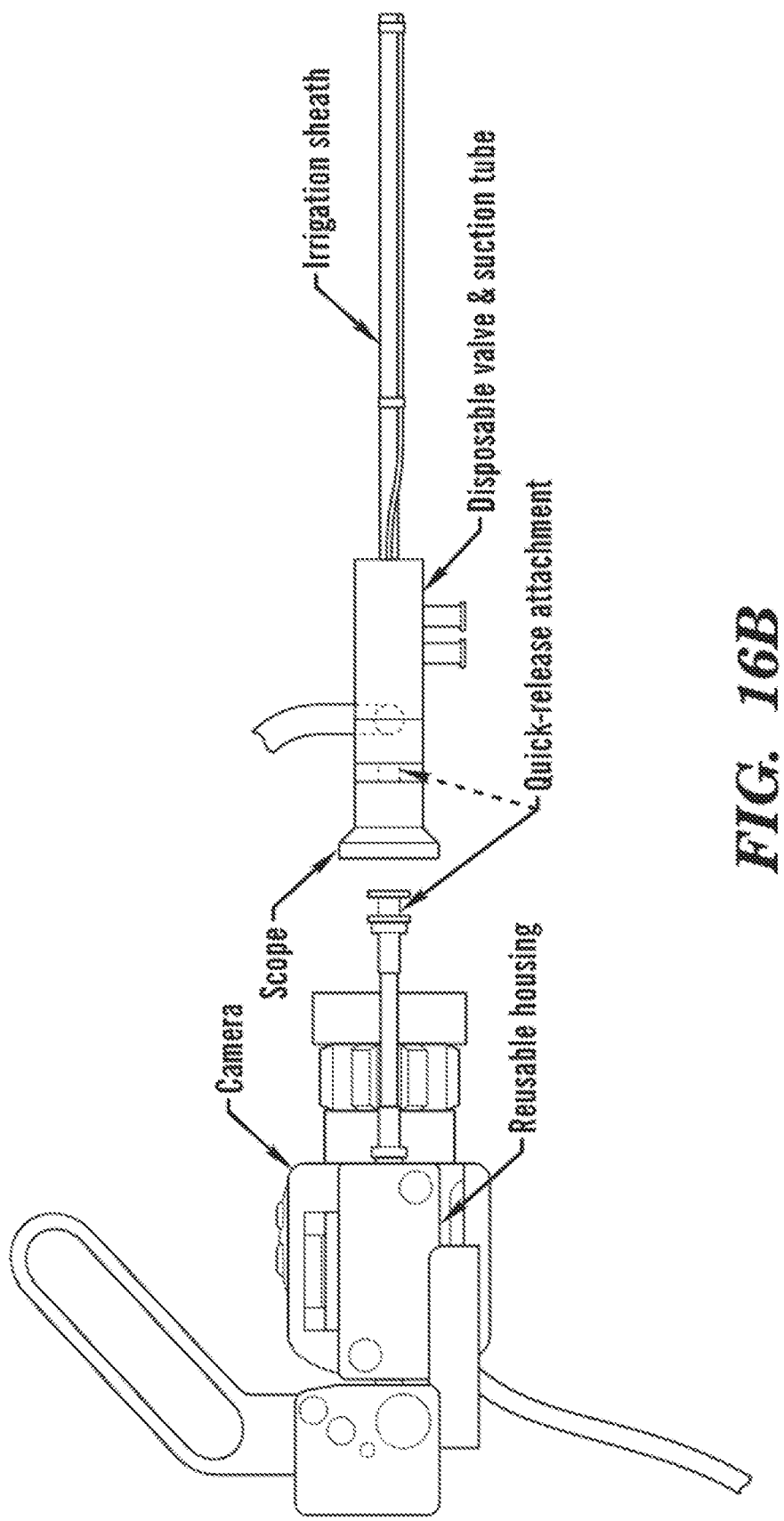
Figure 16C:
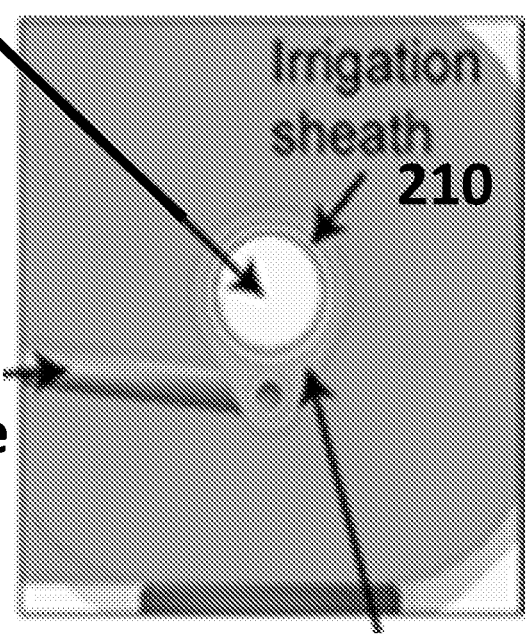
Figure 16D:
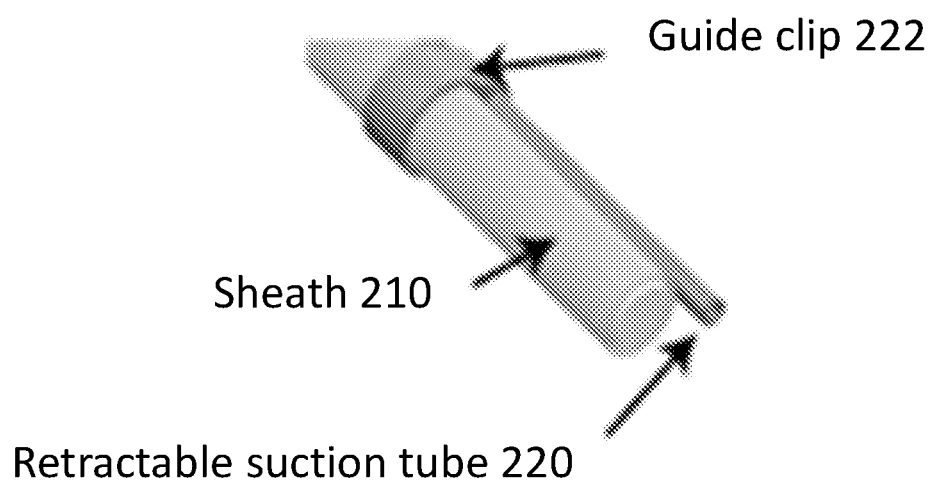

To determine a working configuration of control elements, multiple ergonomic embodiments have been developed, 3D printed and tested one-by-one. In FIG. 7, an embodiment of the actuator is shown. This embodiment has one rotating lever and two buttons and uses the right side of the proximal end of the endoscope for attachment. The rotating lever allows controlled extension of the suction tube and the two buttons are the safety release buttons. Some other embodiments are illustrated side-by-side in FIG. 8. Hand anatomy and range of motion was also taken into consideration for ergonomic design, for example a curved handle can be used in some embodiments, e.g., as depicted in FIG. 16A and 16B.

Figure 9:
FIG. 9 is a photograph of an actuator in accordance with some embodiments of the invention.

One embodiment of the actuator is shown in FIG. 9. The actuator consists of a main block with an external swiveling lever base. The unlocking button is situated on the bottom of the actuator. This means the thumb no longer needs to reach around the aspiration assembly housing, making the button easy to operate. The button was also made large to accommodate different hand sizes and gripping preferences.

Mechanics

Figure 10A:
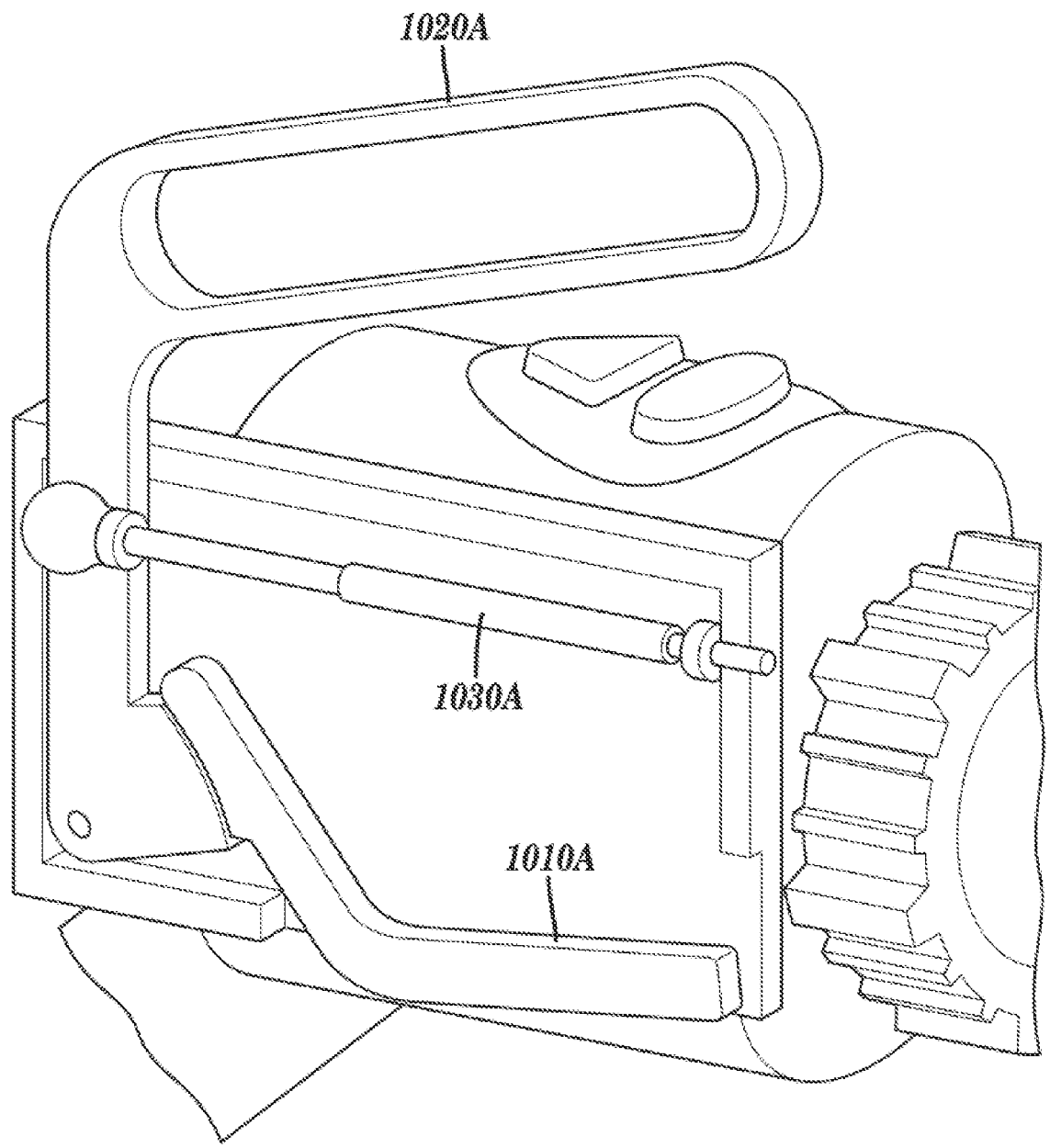
FIGS. 10A-10C are illustrations demonstrating some actuator configurations in accordance with some embodiments of the invention.
Figure 10B:
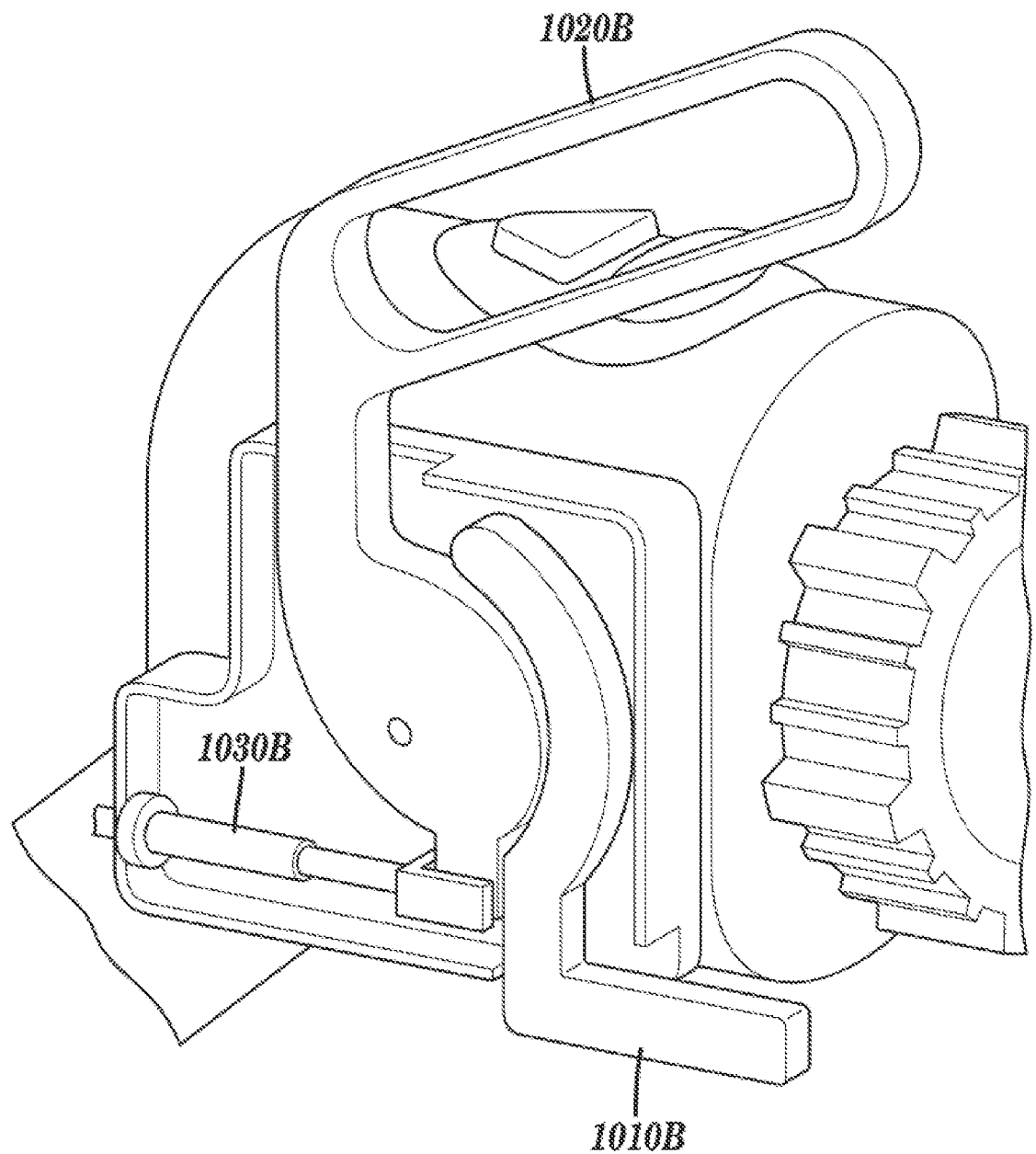
Figure 10C:
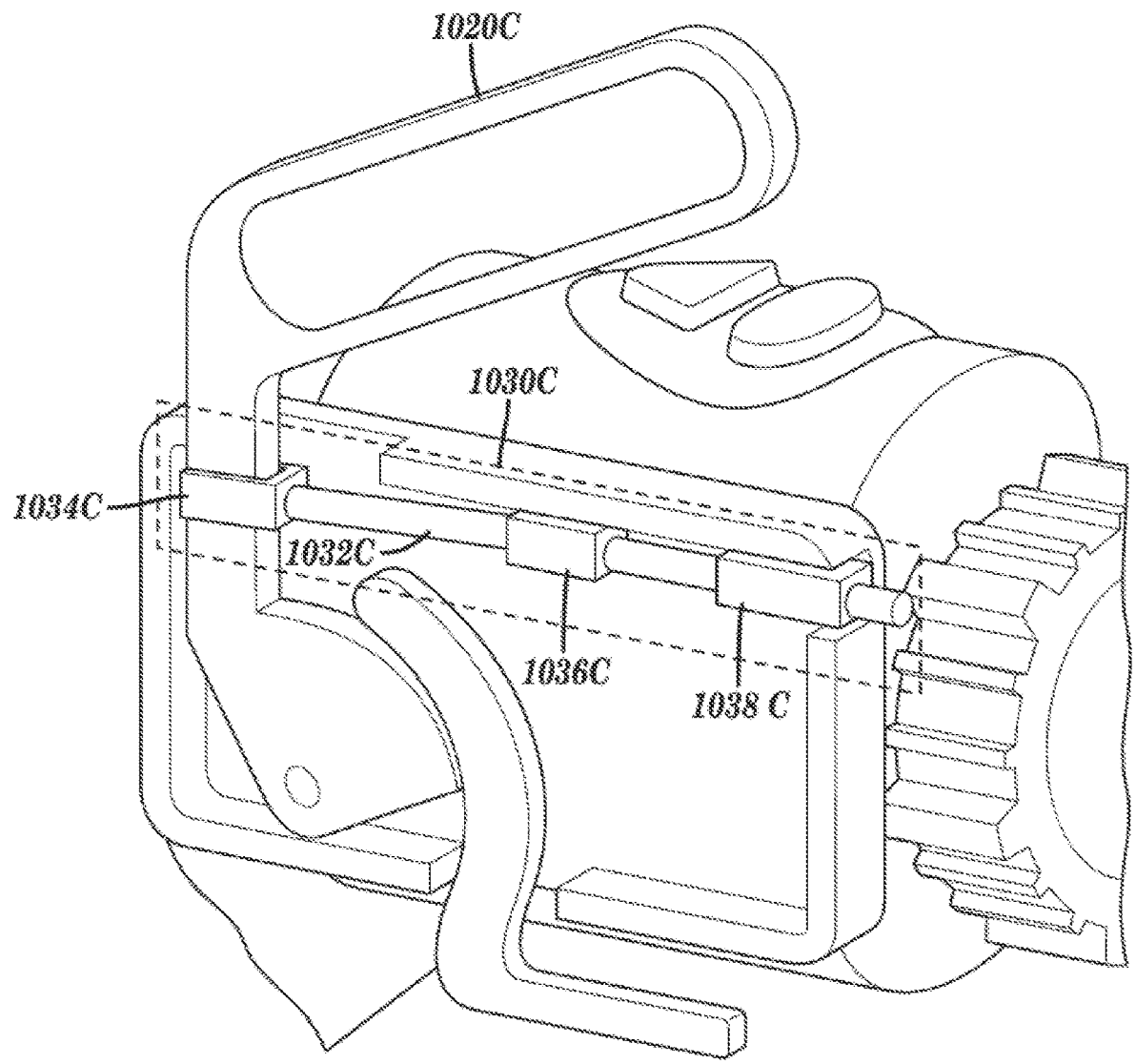

Some embodiments of the actuator are illustrated in FIGS. 10A-10C.

In FIG. 10A, gear teeth are used as a locking mechanism. When the unlocking button 1010A is not pressed upwards, the teeth on the button and lever 1020A intermesh to form a strong lock which prevents lever movement in both directions. The advantage of this is that a relatively weak spring can be used on the unlocking button while still retaining a strong lock, making the unlock button easier to depress and thus preventing fatigue in the thumb. A strong locking system also increases safety as it cannot be easily overpowered, preventing the suction tube from shooting forward when something falls onto the lever. A push-pull cable 1030A is used to connect the linear motion from the actuator to the suction control mechanism. The flexible push-pull cable between the actuator and suction tube or suction control mechanism makes the design broadly applicable for different camera and endoscope combinations.

In FIG. 10B, a friction lock is used instead of a gear lock. The friction lock functions by pushing a surface of an unlocking button 1010B and a surface of a handle portion 1020B together with a spring (not shown). The spring, which is coupled to the unlocking button 1010B, can be positioned such that the unlocking button 1010B is biased to rotate clockwise around its hinge at the top. Surface area for locking can be made as large as possible to optimize locking strength. Interlocking ridges and grooves on the surfaces can be used to improve locking. Sufficient locking strength can lock the handle portion 1020B at a fixed position. The push-pull cable 1030B exits the back and loops around to the front, providing extra flexibility between the actuator and the suction control mechanism.

In FIG. 10C, a pushrod system 1030C is used. Eliminating the push-pull cable from the design means that it can be made completely from stainless steel, making it durable and require less maintenance. In some embodiments, different pushrods would have to be made for almost every different camera-endoscope combination or the pushrod would have to be made adjustable. The pushrod system 1030C uses one or more rods 1032C, two hinging joints 1034C and 1036C, and a linear bearing 1038C to convert the rotary motion of the handle portion 1020C into linear motion inside the actuator. The linear motion of the pushrod system 1030C can be coupled to the suction control mechanism. The pushrod system 1030C is different from the push-pull cable because the former can use bare non-flexible rods to transport the linear motion instead of a flexible cable guided by a flexible sleeve as in the push-pull cable. The pushrod system 1030C can be made from stainless steel which has the benefits of sterilization.

The suction control mechanism is a separate assembly that is attached to the endoscope tip. This forward assembly is responsible for connecting the suction tube to a vacuum source or disconnecting the suction tube from the vacuum source. In FIG. 3, a top down view is given of the endoscope camera setup (ECS) 204 with the aspiration assembly 420 attached thereon. The actuator 410 can be strapped to the camera and the suction control mechanism can be slid over the endoscope tip. The two are designed to be connected with a flexible pull cable similar to a bike's handbrake.

In accordance with some embodiments of the invention, the suction is automatically shut off when the suction tube is fully retracted. FIG. 12 displays a cross-section of an embodiment in accordance with some embodiments of the invention. When the push-pull cable 1230 pulls back on the piston 1240. The piston, suction tube retainer 1250 and suction tube 1260 move backwards until the back wall of the piston meets the back wall on the cylinder, sealing off the canals running through the piston and thus stopping the suction.

In FIG. 2, the mechanism that allows adjusting the handle as in FIG. 9 is combined with a gear locking system. Some of the important features are discussed as follows:

(1) The swiveling handle base has an internal gear transmission that converts the rotary handle motion to a linear motion that lies in the center axis of the swiveling movement. This allows 360 degree rotation of the handle base without affecting the actuation mechanism. The internal mechanism is illustrated in FIG. 6.

(2) Intermeshing gear racks are used to form a strong gear lock. The mechanism and used gear racks are illustrated in FIGS. 5-6. As shown in FIG. 6, when the unlocking button 620 is not pressed, a leaf spring 634 forces the two gear racks to intermesh, forming a solid lock.

Figure 13A:
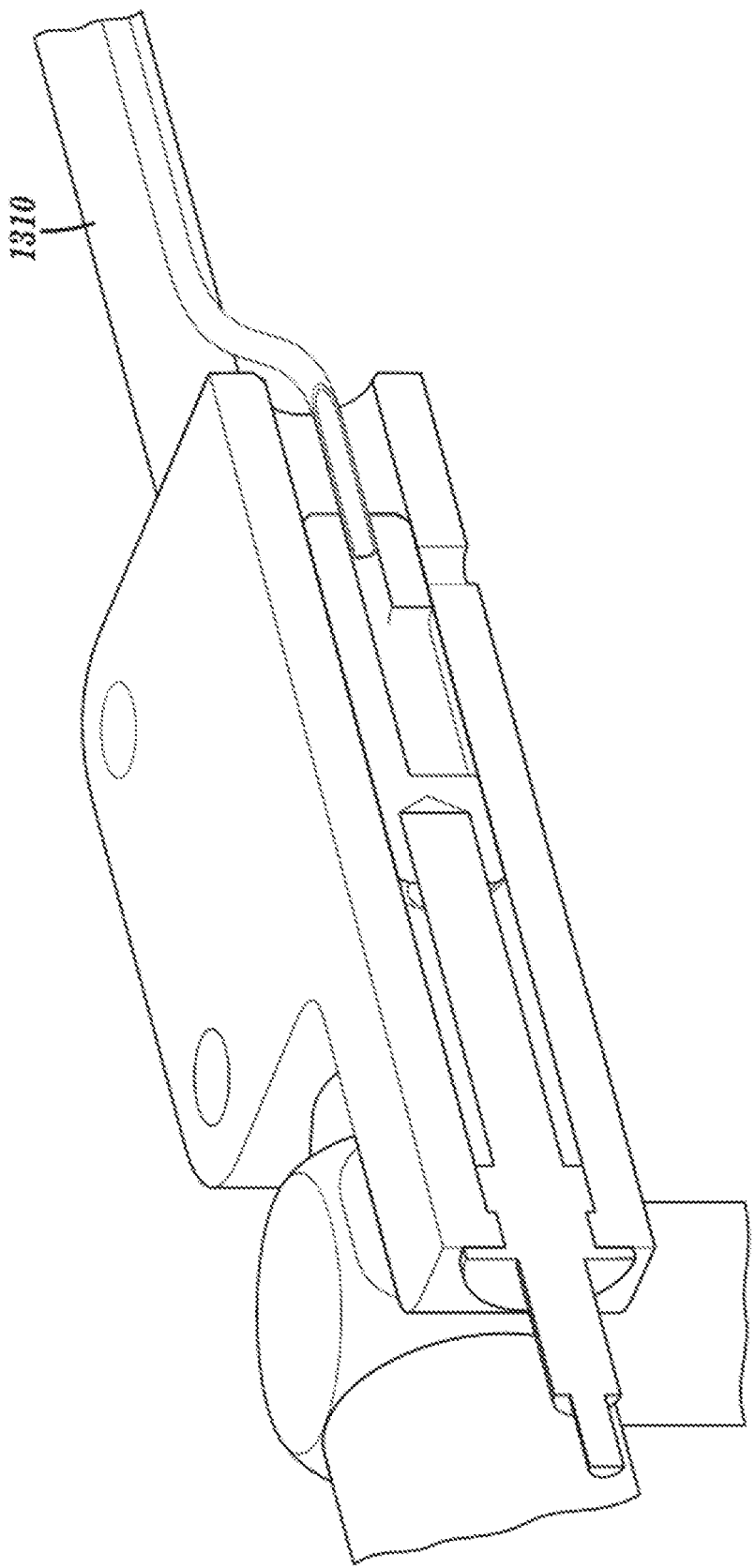
FIGS. 13A and 13B show illustrations of a suction control mechanism that uses a shuffle valve for automatic vacuum shut-off in accordance with some embodiments of the invention.
Figure 13B:
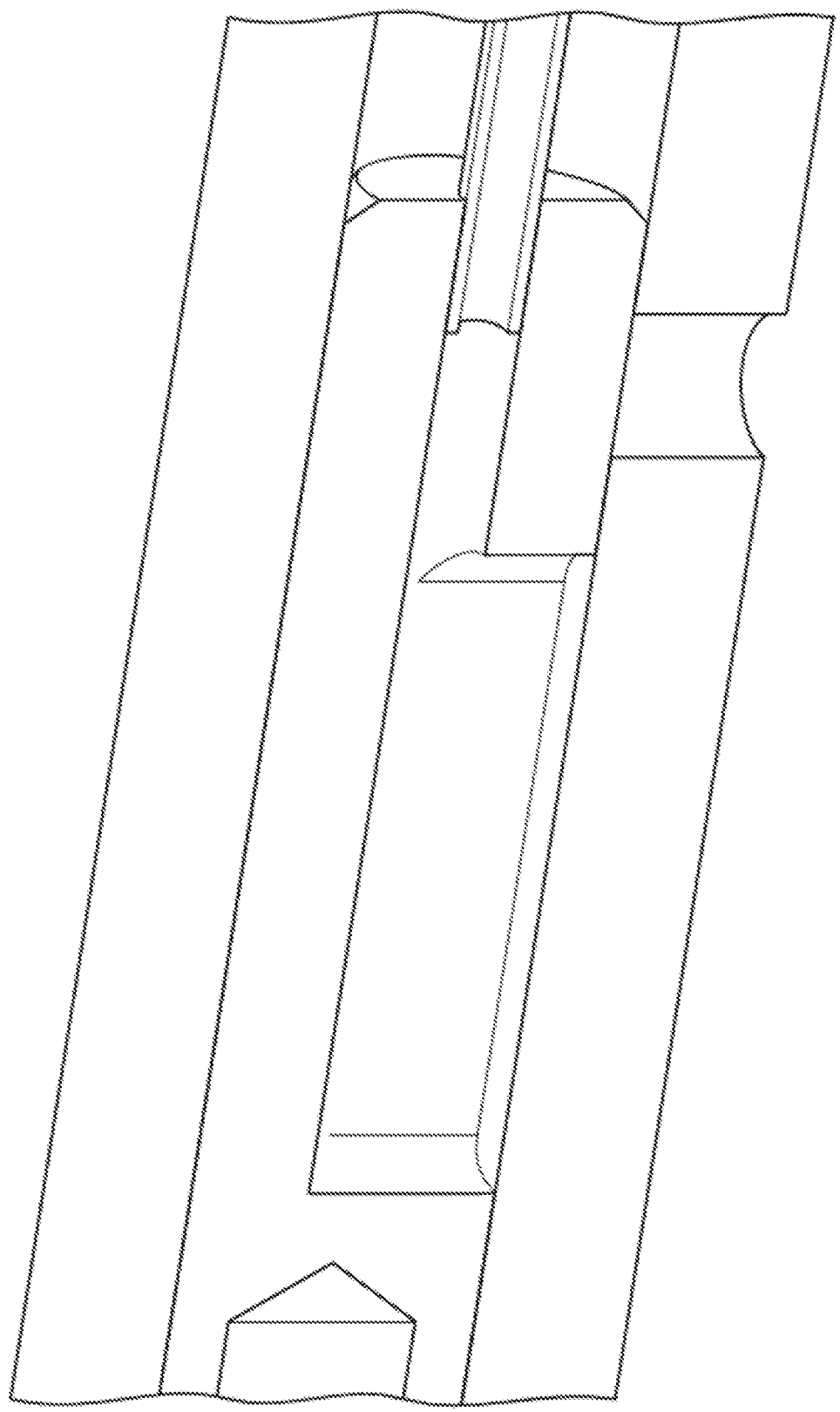

(3) The suction control mechanism is designed so that the push/pull cable can't come in contact with the sucked up matter. Two cross-sections in FIGS. 13A and 13B show a shuffle-valve design. The suction tube is supported by a continuous plastic sheath 1310.

The suction control mechanism is made detachable from the push-pull cable and the actuator. This would allow a surgeon to more quickly change to a different endoscope. Allowing the suction control mechanism to be made disposable can save significant costs associated with cleaning and sterilizing this assembly which has many small channels. To make the suction control mechanism separable from the push-pull cable, a mechanism was conceived that allows quick disconnection without adding more slack to the system.

One embodiment of the invention is illustrated in FIGS. 14A, 14B, 14C. The suction control mechanism can be quickly detached from the push-pull cable 1410 by lifting the retaining ring 1440 up and out of the slot. The rigidity of the push-pull cable 1410 will then also lift the barrel that is swaged to the end of it, out of the cylindrical pocket in the piston 1430, completely separating the cable from the suction control mechanism. The suction control mechanism is shortened, slides further back on the endoscope and uses the friction an O-ring to keep it in place instead of a pinching mechanism. This leaves more usable length on the endoscope and reduces risk of damaging the endoscope.

Lens-cleaning functionality can be integrated into the design. Irrigation fluid can be pumped between the sheath 1450 and endoscope tube to the tip where it can rinse the lens clean. A second Luer-Lock port can be added to the bottom for universal connectivity to an irrigation system.

Results and Discussion

Figure 17:
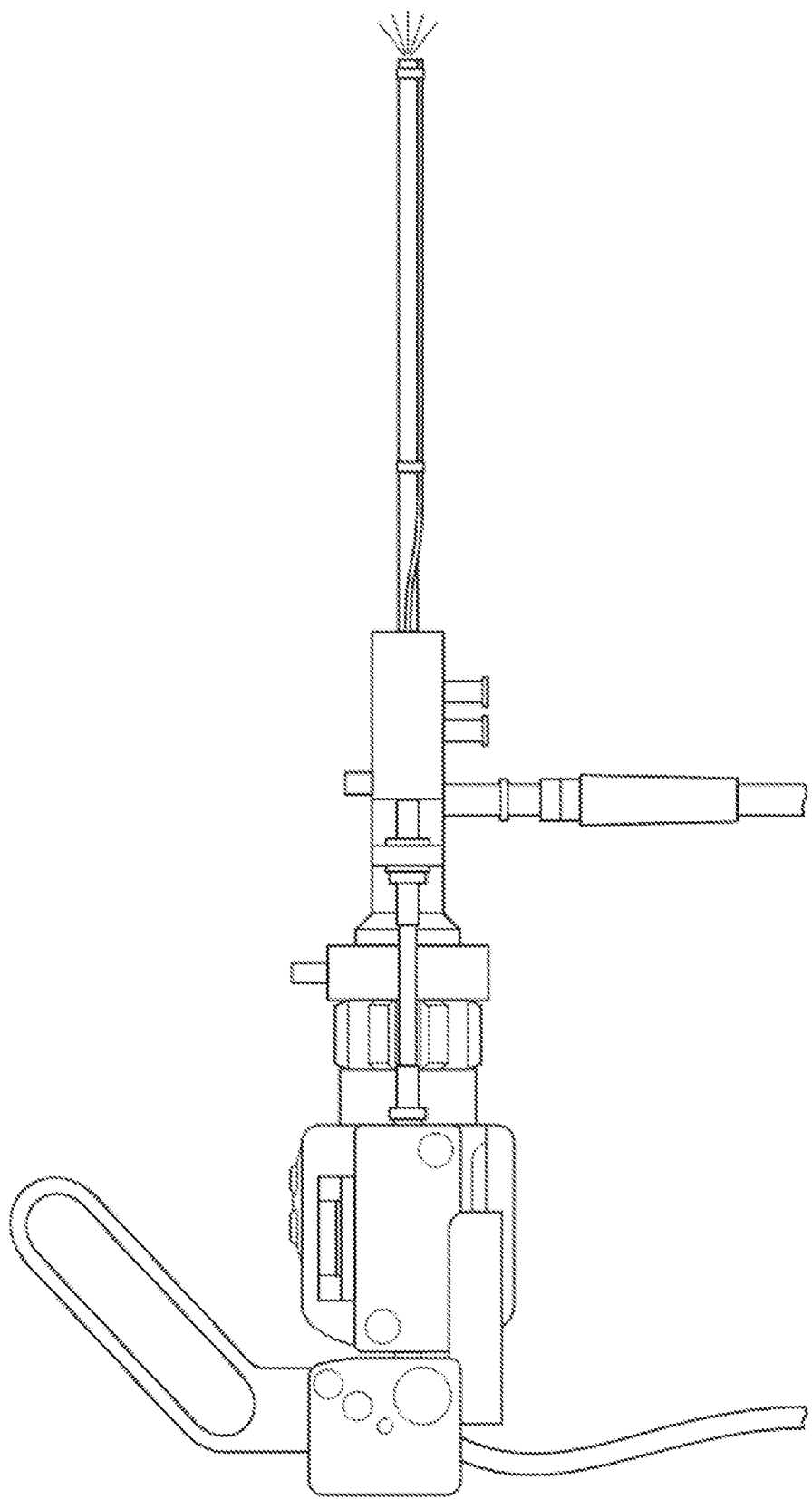
FIG. 17 is a photograph showing an endoscope having an aspiration assembly attached thereon in accordance with some embodiments of the invention. Some portions of the aspiration assembly are made of stainless steel.

Tests were performed on the devices of FIGS. 4A-4C. Tests were also performed on devices comprising metal components (as depicted in FIG. 17). The seals were successful on all embodiments.

Actuation and locking: The actuation and retraction works well. For the actuation test, no O-rings were installed in the suction shut-off valve as they increase friction to a point where the fragile 3D printed gears could break. Use of a metal such as stainless steel can improve the robustness of the mechanical parts. The locking system doesn't slip, even when pressure is applied to the handle. The suction tube extends to the intended maximum point, and retracts fully by pressing the unlocking button and letting the handle retract. The suction control mechanism was tested with O-rings by manually moving the piston. The O-rings caused significant friction as they were not yet lubricated. This can be addressed with medical grade lubricant. Alternatively, the O-ring compression can also be reduced to make the piston move more easily.

Attachment: The endoscope had to be provisionally attached to the camera model to be able to test the attachment of the aspiration assembly. The actuator assembly slipped neatly over the endoscope tip and was held in place with sufficient O-ring friction. The over-center latch allowed easy and firm attachment of the actuator to the camera model. The silicone rubber backing was compressed upon tightening and prevented that the actuator slides around on the side of the camera. The over-center latch is demonstrated in FIGS. 15A and 15B. The quick attachment system between the suction control mechanism and push-pull cable worked well too. A light manual press fit firmly retains the quick attachment ring in the slot. Subsequent attachment to various commercially available cameras confirmed that the attachment approach was versatile. A rubber piece can be substituted for the wire in the over center latch design.

Suction and Lens cleaning: The suction is tested by sucking up water from a cup using a Luer-lock syringe connected to the suction port on the suction control mechanism and pulling back on the plunger. For this test the O-rings are put onto the piston. The lens cleaning functionality is tested by attaching the same syringe to the irrigation port and squeezing water through the irrigation sheath. The suction test proved that the suction works well, 20 ml was removed in 12 seconds by pushing the syringe cylinder away from the plunger with the thumb only. This translates to a flow of approximately 100 mL/min. The lens cleaning system also functions well. Water or irrigation fluid moved through the sheath to the tip of the endoscope. The water or irrigation fluid can be dispersed over the whole lens by surface tension and falls off when droplets reach critical mass. Residual water or irrigation fluid could be removed by retracting the plunger.

What is claimed is:

1. An endoscope system comprising:
    an endoscope comprising a tubular member, a sheath, and at least one irrigation channel:
        the tubular member extending from a proximal end to a distal end, the tubular member including a visualization system configured to transmit images of a field of view from the distal end of the tubular member to a camera coupling at the proximal end of the tubular member;
        the sheath extending circumferentially around the tubular member and having an outer surface extending from the proximal end of the tubular member to the distal end of the tubular member; and
        the one or more irrigation channels inside the sheath and extending from the proximal end of the tubular member to the distal end of the tubular member; and
    an aspiration assembly comprising an extendable suction tube, an actuator, and a locking mechanism;
        wherein the extendable suction tube is removably coupled along the outer surface of the sheath and adapted to, under the control of the actuator, move axially beyond the distal end of the tubular member; and
        the actuator is coupled to the suction tube to extend or retract the suction tube with respect to the distal end of the endoscope when the actuator is actuated, and the locking mechanism is configured to removably attach the extendable suction tube at various axial positions along the outer surface of the sheath and lock the extendable suction tube at a fixed position.

2. The endoscope of claim 1, wherein the extendable suction tube is adapted to, under user control of the actuator, move axially beyond the distal end of the tubular member into the field of view of the visualization system.

3. The endoscope of claim 1, wherein the actuator is removably attached to the proximal end of the endoscope through:
    an over-center latching mechanism; or
    a snap fit.

4. The endoscope system of claim 3, wherein the actuator is not coupled to the camera.

5. The endoscope system of claim 1, wherein the aspiration assembly is removably attached to the endoscope.

6. The endoscope system of claim 1, wherein the suction tube is connected to a vacuum source; and wherein a suction valve is connected between the vacuum source and the suction tube such that when the suction tube is extended, the suction tube is connected by the suction valve to the vacuum source and when the suction tube is retracted, the suction tube is disconnected by the suction valve from the vacuum source.

7. The endoscope system of claim 1, wherein the actuator comprises a movable handle portion coupled to the suction tube such that movement of the handle causes the suction tube to move axially.

8. The endoscope system of claim 1, wherein the actuator comprises a safety button coupled to the locking mechanism and configured to unlock the locking mechanism when the safety button is actuated, thereby permitting the axial movement of the suction tube.

9. The endoscope system of claim 1, further comprising a camera coupled to the proximal end of the tubular member.

10. The endoscope system of claim 1, wherein the actuator is movable circumferentially around the tubular member.

11. The endoscope system of claim 1, further comprising an image guidance system adapter, wherein the extendable suction tube is coupled to the image guidance system adapter and the image guidance system adapter is positioned at a predefined distance from a distal end of the suction tube such that the distal end of the suction tube can be located in an image guidance system.

12. The endoscope system of claim 1, wherein the locking mechanism comprises a pair of gear racks configured to intermesh to lock the suction tube at a fixed axial position.

13. The endoscope system of claim 1, wherein the locking mechanism comprises a friction system to lock the suction tube at a fixed axial position.

* * * * *